(12) United States Patent
Nishio

(10) Patent No.: US 8,895,565 B2
(45) Date of Patent: Nov. 25, 2014

(54) HETEROCYCLIC COMPOUND AND USE OF THE SAME

(76) Inventor: Tetsuya Nishio, Tokyo (JP)

( * ) Notice: Subject to any disclaimer, the term of this patent is extended or adjusted under 35 U.S.C. 154(b) by 13 days.

(21) Appl. No.: 13/201,201

(22) PCT Filed: Feb. 8, 2010

(86) PCT No.: PCT/JP2010/052126
§ 371 (c)(1),
(2), (4) Date: Aug. 11, 2011

(87) PCT Pub. No.: WO2010/064737
PCT Pub. Date: Jun. 10, 2010

(65) Prior Publication Data
US 2011/0319618 A1 Dec. 29, 2011

(30) Foreign Application Priority Data

Feb. 16, 2009 (JP) ................. 2009-055661
May 13, 2009 (JP) ................. 2009-133491
May 20, 2009 (JP) ................. 2009-138659
Jun. 10, 2009 (JP) ................. 2009-156146
Jan. 4, 2010 (JP) ................. 2010-011405

(51) Int. Cl.
C07D 239/42 (2006.01)
A61K 31/341 (2006.01)
C07D 405/12 (2006.01)

(52) U.S. Cl.
CPC ............ *C07D 239/42* (2013.01); *C07D 405/12* (2013.01)
USPC ............................. 514/256; 544/328; 544/329

(58) Field of Classification Search
USPC .................................. 544/328, 329; 514/256
See application file for complete search history.

(56) References Cited

U.S. PATENT DOCUMENTS 6,140,351 A * 10/2000 Arnaiz et al. ................. 514/336
2008/0287468 A1 11/2008 Ohlmeyer et al.

FOREIGN PATENT DOCUMENTS

| GB | 901749 | 7/1962 |
|---|---|---|
| JP | 10-087492 A | 4/1998 |
| WO | WO 92/18498 A1 | 10/1992 |
| WO | WO 2004/056786 A2 | 7/2004 |
| WO | WO 2005/092899 A1 | 10/2005 |
| WO | WO 2007/042571 A1 | 4/2007 |
| WO | WO 2007/044813 A1 | 4/2007 |
| WO | WO 2008/113255 A1 | 9/2008 |
| WO | WO 2008/115742 A1 | 9/2008 |
| WO | WO 2008/129380 A1 | 10/2008 |

OTHER PUBLICATIONS

International Preliminary Report on Patentability noticed Aug. 25, 2011, in International Patent Application No. PCT/JP2010/052126.
Chemical Handbook, Applied Chemistry, Sixth Edition, pp. 1401-1403, edited by Chemical Society of Japan, issued by Maruzen, (2003).
Carpenter et al., "Rapid Enhancement of Protein Phosphorylation in A-431 Cell Membrane Preparations by Epidermal Growth Factor", J. Biol. Chem., vol. 254, No. 11, Jun. 10, 1979, pp. 4884-4891.
Cohen et. al., "A Native 170,000 Epidermal Growth Factor Receptor-Kinase Complex from Shed Plasma Membrane Vesicles", J. Biol. Chem., vol. 257, No. 3, Feb. 10, 1982, pp. 1523-1531.
Braun et al., "Synthetic Tyrosine Polymers As Substrates and Inhibitors of Tyrosine-specific Protein Kinases", J. Biol. Chem., vol. 259, No. 4, Feb. 25, 1984, pp. 2051-2054.
Goldsworthy et al., "Guidelines for Measuring Chemically Induced Cell Proliferation in Specific Rodent Target Organs", Chemically Induced Cell Proliferation: Implications for Risk Assessment, Wiley-Liss Inc., 1991, pp. 253-284.

* cited by examiner

*Primary Examiner* — Deepak Rao
(74) *Attorney, Agent, or Firm* — Miles & Stockbridge P.C.

(57) ABSTRACT

Provided is a compound represented by general formula (6) and pharmaceutically acceptable salts thereof. (In the formula, $R^1$ is a hydrogen atom or a $C_{1-6}$ alkyl group; $R^2$ is a hydrogen atom or a $C_{1-6}$ alkyl group; $R^3$ is a hydrogen atom, a halogen atom, a $C_{1-6}$ alkyl group, or a $C_{1-6}$ haloalkyl group.)

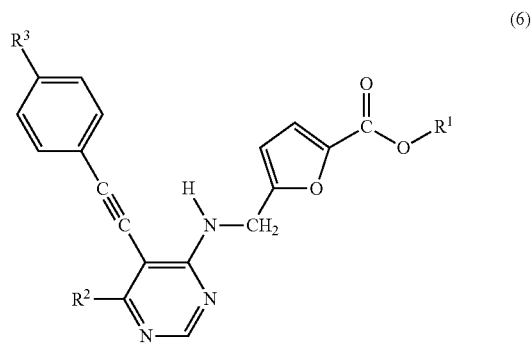

(6)

19 Claims, No Drawings

HETEROCYCLIC COMPOUND AND USE OF THE SAME

TECHNICAL FIELD

The present invention relates to a heterocyclic compound useful as agents for medical or other uses, in particular as specific kinds of medicaments including anticancer agents and/or tyrosine kinase inhibitors, and also to specific uses of the compound. The present invention further relates to a pharmaceutical composition containing such a heterocyclic compound, and uses thereof in the production of anticancer agents for warm-blooded animals (e.g., humans), and/or in the treatment of various diseases in which abnormal activities of tyrosine kinases are involved, which include, for example, diseases associated with cell proliferation (esp., cancer cell proliferation), vascularization and/or increased vascular permeability.

BACKGROUND ART

Typical anticancer agents presently available include, for example, alkylating agents, antimetabolites, molecular-targeted drugs, platinum drugs, plant-derived anticancer agents, anticancer antibiotics, BRM (biological response modifiers), cancer vaccines, cytokines, differentiation-inducing agents, monoclonal antibodies and hormonal anticancer agents.

Among the above anticancer agents, those that are biologicals have difficulties in large-scale production and cost along with a long period of time required for producing them. On the other hand, anticancer agents which are chemically synthesized using a rare metal have also difficulties in cost and large-scale production.

Recently, to solve the above problems, anticancer agents that can be chemically synthesized at a reasonable cost have been attracting attention. Among such anticancer agents, tyrosine kinase inhibitors, serving as a molecular-targeted drug, are expected to be useful as a therapeutic and/or prophylactic agent. Tyrosine kinase inhibitors inhibit the action of tyrosine kinases which promotes phosphorylation of tyrosine that is a specific amino acid contained in proteins (e.g., inhibiting autophosphorylation by tyrosine kinases), thereby suppressing the growth of cancer. Various tyrosine kinases are known, which include those of receptor type such as platelet-derived growth factor (PDGF) receptors, fibroblast growth factor (FGF) receptors, epidermal growth factor (EGF) receptors and the like, as seen in Non-patent Literature 1. While these receptors are involved in cancer growth signals, HER2 is also known as a similar factor. Specifically, HER2 (human EGF receptor 2) gene is a gene for a transmembrane receptor glycoprotein. This receptor is also involved in tyrosine kinase activities. See Non-patent Literature 1. Further, epidermal growth factor (EGF) and vascular endothelial growth factor (VEGF) are involved in vascularization. These molecular-targeted drugs are also effective as an inhibitor for the activity of Abl tyrosine kinases, for example, as an inhibitor for the activity of Bcr-Abl kinase that is a protein causing chronic myelocytic leukemia (CML). Moreover, these molecular-targeted drugs are useful as prophylactic agents for preventing malignant transformation of cancer (e.g., acquisition of an infiltration ability and/or a metastatic ability by cancer cells) and canceration of cells (conversion of normal cells into cancer cells), which include, for example, a prophylactic agent for preventing transformation of hormone-dependent cancers such as one dependent on LH-RH (luteinizing hormone releasing hormone) into hormone-independent cancers, a prophylactic agent inducing apoptosis of cells to be transformed into cancer cells, and a prophylactic agent serving as an antioxidant for preventing transformation into cancer.

It is pointed out that tyrosine kinases are also involved in diseases other than cancer, which include, for example, diseases associated with inflammation or allergy (such as pollinosis, allergic rhinitis, allergic asthma, bronchial asthma, rhinitis, atopic dermatitis and the like), diabetes, and Alzheimer's disease. It is further pointed out that tyrosine kinases are associated with anticancer agents, anti-inflammatory agents, etc. While action mechanisms of tyrosine kinase inhibitors are still mostly unclear, some of those action mechanisms have recently been elucidated based on the chemical structure of them. These tyrosine kinase inhibitors include low molecular weight compounds and in such cases, large-scale production would be relatively easy. Accordingly, it is expected that many companies will enter this field of pharmaceutical products in the future.

However, presently available tyrosine kinase inhibitors have many problems. First, tyrosine kinase inhibitors presently on the market as a molecular-targeted drug show therapeutic performances which drastically vary depending upon patients. Second, drug resistance against those inhibitors can easily be developed.

Under the above circumstances, the present invention aims at providing a novel heterocyclic compound to be contained, particularly as an anticancer agent, in a pharmaceutical composition.

CITATION LIST

Non Patent Literature 1: "Chemical Handbook, Applied Chemistry, Sixth Edition", pp. 1401-1403, edited by Chemical Society of Japan, issued by Maruzen.

SUMMARY OF INVENTION

Technical Problem

The problem to be solved by the invention is to provide an anticancer agent having an excellent anticancer activity and/or a tyrosine kinase inhibitory activity regardless of individual differences along with low toxicity as well as good solubility and absorbability.

Solution to Problem

The inventor of the present invention intensively studied on anticancer agents and/or tyrosine kinase inhibitors. As a result, the inventor has found that specific heterocyclic compounds provided accurately in accordance with the molecular design of the present invention will show a satisfactory anti-tumor activity as well as low toxicity, hence being potentially used as an anticancer agent (e.g., a therapeutic or prophylactic agent for cancer) with a wide safety margin and/or a therapeutic or prophylactic utility for diseases in which tyrosine kinases are involved, thereby having made the present invention.

More specifically, the present invention relates, non-restrictively, to (1) A compound represented by general formula (1):

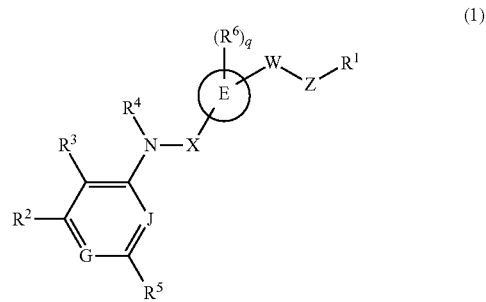

wherein q is an integer selected from 0, 1, 2, 3 and 4; $R^1$ is a hydrogen atom, a halogen atom, a $C_{1-6}$ alkyl group, a $C_{1-6}$ haloalkyl group, a $C_{3-8}$ cycloalkyl group, a $C_{2-6}$ alkenyl group, a $C_{2-6}$ alkynyl group, a $C_{1-6}$ alkoxy $C_{1-6}$ alkyl group, an aralkyl group which may have one or more substituents, an aryl group which may have one or more substituents, an amino $C_{1-6}$ alkyl group which may have one or more substituents, a heterocyclic group which may have one or more substituents, or a heterocyclic $C_{1-6}$ alkyl group which may have one or more substituents; $R^2$ is a hydrogen atom, a halogen atom, a $C_{1-6}$ alkyl group, a $C_{1-6}$ haloalkyl group, a $C_{3-8}$ cycloalkyl group, a $C_{1-6}$ alkoxy $C_{1-6}$ alkyl group, a $C_{1-6}$ alkoxy group, an aryl group which may have one or more substituents, an aryl $C_{2-6}$ alkynyl group which may have one or more substituents, a $C_{2-6}$ alkynyl group which may have one or more substituents, a $C_{2-6}$ alkenyl group which may have one or more substituents, or an aryl $C_{2-6}$ alkenyl group which may have one or more substituents; $R^3$ is a hydrogen atom, a nitro group, a cyano group, a carbamoyl group, a $C_{1-6}$ haloalkyl group, a $C_{1-6}$ alkoxy group, a $C_{1-6}$ alkoxy $C_{1-6}$ alkyl group, a $C_{2-6}$ alkynyl group which may have one or more substituents, an aryl $C_{2-6}$ alkynyl group which may have one or more substituents, a $C_{2-6}$ alkenyl group which may have one or more substituents, an aryl $C_{2-6}$ alkenyl group which may have one or more substituents, a $C_{3-6}$ cycloalkenyl group, a $C_{4-6}$ cycloalkadienyl group, or a heterocyclic group which may have one or more substituents; $R^4$ is a hydrogen atom, a $C_{1-6}$ alkyl group, or a $C_{3-8}$ cycloalkyl group; $R^5$ is a hydrogen atom, a $C_{1-6}$ alkyl group, a $C_{3-8}$ cycloalkyl group, a $C_{1-6}$ alkoxy group, a $C_{1-6}$ alkylsulfanyl group, a $C_{1-6}$ alkylsulfinyl group, a $C_{1-6}$ alkylsulfonyl group, an amino group which may have one or more substituents, a $C_{1-6}$ haloalkyl group, a halogen atom, an aralkyl group which may have one or more substituents, a $C_{2-6}$ alkynyl group which may have one or more substituents, an aryl $C_{2-6}$ alkynyl group which may have one or more substituents, a $C_{2-6}$ alkenyl group which may have one or more substituents, an aryl $C_{2-6}$ alkenyl group which may have one or more substituents, a heterocyclic group which may have one or more substituents, or an aryl group which may have one or more substituents; $R^6$ is independently a $C_{1-6}$ alkoxy group, a halogen atom, a nitro group, a $C_{2-6}$ alkynyl group which may have one or more substituents, or a $C_{1-6}$ alkyl group; G and J are each independently a nitrogen atom, or a $CR^7$ where $R^7$ is, independently for each occurrence, a hydrogen atom or a $C_{1-6}$ alkyl group, W is a single bond, C(O), S(O), S(O)$_2$ or an oxygen atom; X is a $C_{1-6}$ alkylene group; Z is a single bond, an oxygen atom, O(CH$_2$)O, O(CH$_2$CH$_2$)O, O(CH$_2$CH$_2$CH$_2$)O, O(CH$_2$)C(O), O(CH$_2$CH$_2$)C(O), O(CH$_2$CH$_2$CH$_2$)C(O), NH, N(CH$_3$), or N(C$_2$H$_5$); and ring E is a benzene ring, a furan ring, a thiophene ring, a pyridine ring, a pyrrole ring, a cyclohexane ring, or a naphthalene ring, or a pharmaceutically acceptable salt thereof;

(2) A compound represented by general formula (2):

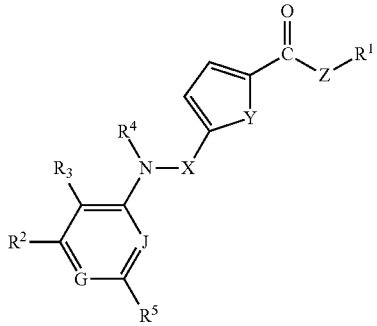

wherein $R^1$ is a hydrogen atom, a halogen atom, a $C_{1-6}$ alkyl group, a $C_{3-8}$ cycloalkyl group, a $C_{2-6}$ alkenyl group, a $C_{2-6}$ alkynyl group, an aralkyl group which may have one or more substituents, a $C_{1-6}$ alkoxy $C_{1-6}$ alkyl group, an aryl group which may have one or more substituents, an amino $C_{1-6}$ alkyl group which may have one or more substituents, a heterocyclic group which may have one or more substituents, or a heterocyclic $C_{1-6}$ alkyl group which may have one or more substituents; $R^2$ is a hydrogen atom, a halogen atom, a $C_{1-6}$ alkyl group, a $C_{1-6}$ haloalkyl group, a $C_{3-8}$ cycloalkyl group, a $C_{1-6}$ alkoxy $C_{1-6}$ alkyl group, a $C_{1-6}$ alkoxy group, an aryl group which may have one or more substituents, a $C_{2-6}$ alkynyl group which may have one or more substituents, an aryl $C_{2-6}$ alkynyl group which may have one or more substituents, a $C_{2-6}$ alkenyl group which may have one or more substituents, or an aryl $C_{2-6}$ alkenyl group which may have one or more substituents; $R^3$ is a hydrogen atom, a halogen atom, a nitro group, a cyano group, a carbamoyl group, a carboxyl group, a $C_{1-6}$ alkyl group, a $C_{1-6}$ haloalkyl group, a $C_{1-6}$ alkoxy group, a $C_{1-6}$ alkoxy $C_{1-6}$ alkyl group, a $C_{1-6}$ alkoxycarbonyl group, a $C_{2-6}$ alkynyl group which may have one or more substituents, an aryl $C_{2-6}$ alkynyl group which may have one or more substituents, a $C_{2-6}$ alkenyl group which may have one or more substituents, an aryl $C_{2-6}$ alkenyl group which may have one or more substituents, a heterocyclic group which may have one or more substituents, or an aryl group which may have one or more substituents; $R^4$ is a hydrogen atom, a $C_{1-6}$ alkyl group, or a $C_{3-8}$ cycloalkyl group; $R^5$ is a hydrogen atom, a $C_{1-6}$ alkyl group, a $C_{3-8}$ cycloalkyl group, a $C_{1-6}$ alkoxy group, a $C_{1-6}$ alkylsulfanyl group, a $C_{1-6}$ alkylsulfinyl group, a $C_{1-6}$ alkylsulfonyl group, an amino group which may have one or more substituents, a $C_{1-6}$ haloalkyl group, a halogen atom, an aralkyl group which may have one or more substituents, a $C_{2-6}$ alkynyl group which may have one or more substituents, an aryl $C_{2-6}$ alkynyl group which may have one or more substituents, a $C_{2-6}$ alkenyl group which may have one or more substituents, an aryl $C_{2-6}$ alkenyl group which may have one or more substituents, a heterocyclic group which may have one or more substituents, or an aryl group which may have one or more substituents; G is a nitrogen atom or CH; J is a nitrogen atom or CH; X is a $C_{1-6}$ alkylene group; Y is an oxygen atom, a sulfur atom, or NH; and Z is a single bond, an oxygen atom, O(CH$_2$)O, O(CH$_2$CH$_2$)O, O(CH$_2$CH$_2$CH$_2$)O, O(CH$_2$)C(O), O(CH$_2$CH$_2$)C(O), O(CH$_2$CH$_2$CH$_2$)C(O), NH, N(CH$_3$), or N(C$_2$H$_5$), or a pharmaceutically acceptable salt thereof;

(3) A compound represented by general formula (3):

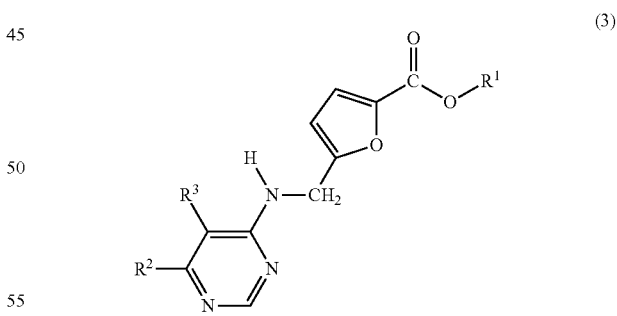

wherein $R^1$ is a hydrogen atom, a $C_{1-6}$ alkyl group, a $C_{3-8}$ cycloalkyl group, a $C_{2-6}$ alkenyl group, a $C_{2-6}$ alkynyl group, or an aralkyl group which may have one or more substituents; $R^2$ is a hydrogen atom, a halogen atom, a $C_{1-6}$ alkyl group, a $C_{1-6}$ haloalkyl group, a $C_{1-6}$ alkoxy $C_{1-6}$ alkyl group, a $C_{1-6}$ alkoxy group, an aryl group which may have one or more substituents, a $C_{2-6}$ alkynyl group which may have one or more substituents, an aryl $C_{2-6}$ alkynyl group which may have one or more substituents, a $C_{2-6}$ alkenyl group which may have one or more substituents, or an aryl $C_{2-6}$ alkenyl group which may have one or more substituents; and $R^3$ is a hydrogen atom, a halogen atom, a cyano group, a carbamoyl group, a carboxyl group, a $C_{1-6}$ alkyl group, a $C_{1-6}$ haloalkyl group, a $C_{1-6}$ alkoxy group, a $C_{1-6}$ alkoxycarbonyl group, a $C_{2-6}$ alkynyl group which may have one or more substituents, an aryl $C_{2-6}$ alkynyl group which may have one or more substituents, an aryl $C_{2-6}$ alkenyl group which may have one or more substituents, a $C_{2-6}$ alkenyl group which may have one or more substituents, or an aryl group which may have one or more substituents, or a pharmaceutically acceptable salt thereof;

(4) A compound represented by general formula (4):

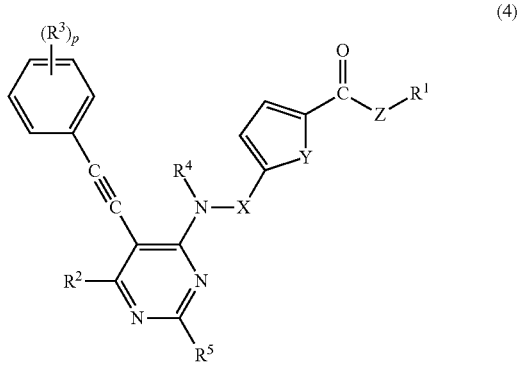

(4)

wherein p is an integer selected from 0, 1, 2 and 3; $R^1$ is a hydrogen atom, a $C_{1-6}$ alkyl group, a $C_{3-8}$ cycloalkyl group, a $C_{2-6}$ alkenyl group, a $C_{2-6}$ alkynyl group, an aralkyl group which may have one or more substituents, an amino $C_{1-6}$ alkyl group which may have one or more substituents, a heterocyclic group which may have one or more substituents, or a heterocyclic $C_{1-6}$ alkyl group which may have one or more substituents; $R^2$ is a hydrogen atom, a $C_{1-6}$ alkyl group, a $C_{1-6}$ haloalkyl group, or a halogen atom; $R^3$ is independently a halogen atom, a $C_{1-6}$ haloalkyl group, a $C_{1-6}$ alkyl group, a $C_{1-6}$ alkoxy group, or a $C_{1-6}$ haloalkoxy group; $R^4$ is a hydrogen atom or a $C_{1-6}$ alkyl group; $R^5$ is a hydrogen atom, a $C_{1-6}$ alkyl group, a $C_{3-8}$ cycloalkyl group, a $C_{1-6}$ haloalkyl group, or a halogen atom; X is a $C_{1-6}$ alkylene group; Y is an oxygen atom or a sulfur atom; and Z is a single bond, an oxygen atom, $O(CH_2)O$, $O(CH_2CH_2)O$, $O(CH_2)C(O)$, $O(CH_2CH_2)C(O)$, NH, $N(CH_3)$, or $N(C_2H_5)$, or a pharmaceutically acceptable salt thereof;

(5) The compound or a pharmaceutically acceptable salt thereof according to the above item (4), in which $R^1$ is a hydrogen atom or a $C_{1-6}$ alkyl group; $R^2$ is a hydrogen atom or a $C_{1-6}$ alkyl group; $R^3$ is a halogen atom, a $C_{1-6}$ haloalkyl group, or a $C_{1-6}$ alkyl group; $R^5$ is a hydrogen atom or a $C_{1-6}$ alkyl group; and Z is an oxygen atom;

(6) A compound represented by general formula (5):

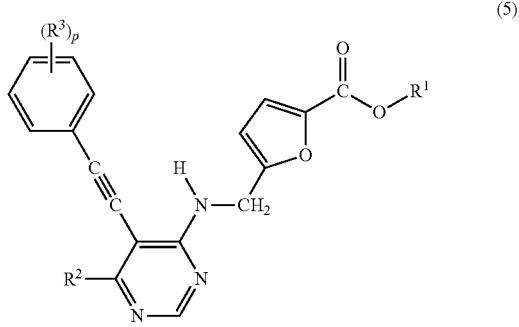

(5)

wherein p is an integer selected from 0, 1, 2 and 3; $R^1$ is a hydrogen atom or a $C_{1-6}$ alkyl group; $R^2$ is a hydrogen atom, a halogen atom, a $C_{1-6}$ alkyl group, or a $C_{1-6}$ haloalkyl group; and $R^3$ is independently a halogen atom, a $C_{1-6}$ alkyl group, or a $C_{1-6}$ haloalkyl group, or a pharmaceutically acceptable salt thereof;

(7) The compound or a pharmaceutically acceptable salt thereof according to the above item (6), in which $R^2$ is a hydrogen atom or a $C_{1-6}$ alkyl group;

(8) A compound represented by general formula (6):

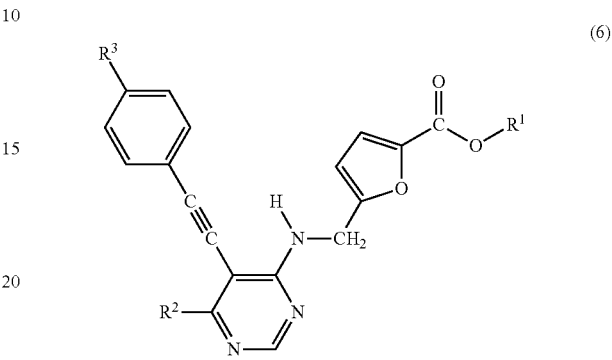

(6)

wherein $R^1$ is a hydrogen atom or a $C_{1-6}$ alkyl group; $R^2$ is a hydrogen atom or a $C_{1-6}$ alkyl group; and $R^3$ is a hydrogen atom, a halogen atom, a $C_{1-6}$ alkyl group, or a $C_{1-6}$ haloalkyl group, or a pharmaceutically acceptable salt thereof;

(9) The compound or a pharmaceutically acceptable salt thereof according to any one of the above items (4) to (8), in which $R^1$ is a $C_{1-6}$ alkyl group; $R^2$ is a $C_{1-6}$ alkyl group; and $R^3$ is a halogen atom or a $C_{1-6}$ haloalkyl group;

(10) The compound or a pharmaceutically acceptable salt thereof according to any one of the above items (4) to (8), in which $R^1$ is a methyl group or an ethyl group; $R^2$ is a methyl group or an ethyl group; and $R^3$ is a fluorine atom, a chlorine atom, or a trifluoromethyl group;

(11) A compound represented by general formula (7):

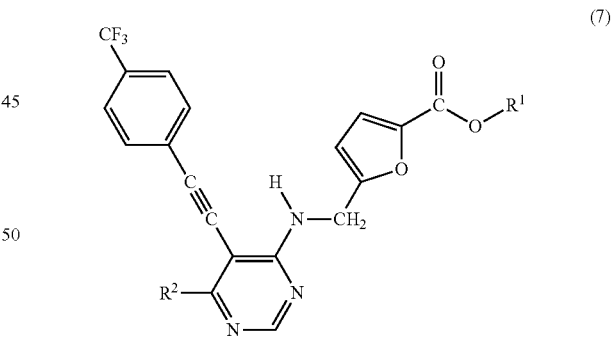

(7)

wherein $R^1$ is a methyl group or an ethyl group; and $R^2$ is a methyl group or an ethyl group, or a pharmaceutically acceptable salt thereof;

(12) At least one compound selected from the group consisting of:
methyl 5-(6-methyl-5-{[4-(trifluoromethyl)phenyl]ethynyl}pyrimidin-4-ylaminomethyl)-2-furancarboxylate; and
ethyl 5-(6-methyl-5-{[4-(trifluoromethyl)phenyl]ethynyl}pyrimidin-4-ylaminomethyl)-2-furancarboxylate, or
a pharmaceutically acceptable salt thereof;

(13) At least one compound selected from the group consisting of:
methyl 4-(6-methyl-5-{[4-(trifluoromethyl)phenyl]ethynyl}pyrimidin-4-ylaminomethyl)benzoate; and
ethyl 4-(6-methyl-5-{[4-(trifluoromethyl)phenyl]ethynyl}pyrimidin-4-ylaminomethyl)benzoate, or
a pharmaceutically acceptable salt thereof;

(14) At least one compound selected from the group consisting of:
methyl 5-(5-{[4-(trifluoromethyl)phenyl]ethynyl}pyrimidin-4-ylaminomethyl)-2-furancarboxylate;
ethyl 5-(5-{[4-(trifluoromethyl)phenyl]ethynyl}pyrimidin-4-ylaminomethyl)-2-furancarboxylate;
methyl 4-(5-{[4-(trifluoromethyl)phenyl]ethynyl}pyrimidin-4-ylaminomethyl)benzoate; and
ethyl 4-(5-{[4-(trifluoromethyl)phenyl]ethynyl}pyrimidin-4-ylaminomethyl)benzoate, or
a pharmaceutically acceptable salt thereof;

(15) At least one compound selected from the group consisting of:
methyl 5-(2-isopropyl-6-methyl-5-{[4-(trifluoromethyl)phenyl]ethynyl}pyrimidin-4-ylaminomethyl)-2-furancarboxylate;
ethyl 5-(2-isopropyl-6-methyl-5-{[4-(trifluoromethyl)phenyl]ethynyl}pyrimidin-4-ylaminomethyl)-2-furancarboxylate;
methyl 5-(2,6-dimethyl-5-{[4-(trifluoromethyl)phenyl]ethynyl}pyrimidin-4-ylaminomethyl)-2-furancarboxylate; and
ethyl 5-(2,6-dimethyl-5-{[4-(trifluoromethyl)phenyl]ethynyl}pyrimidin-4-ylaminomethyl)-2-furancarboxylate, or
a pharmaceutically acceptable salt thereof;

(16) At least one compound selected from the group consisting of:
methyl 4-(2-isopropyl-6-methyl-5-{[4-(trifluoromethyl)phenyl]ethynyl}pyrimidin-4-ylaminomethyl)benzoate;
ethyl 4-(2-isopropyl-6-methyl-5-{[4-(trifluoromethyl)phenyl]ethynyl}pyrimidin-4-ylaminomethyl)benzoate;
methyl 4-(2,6-dimethyl-5-{[4-(trifluoromethyl)phenyl]ethynyl}pyrimidin-4-ylaminomethyl)benzoate; and
ethyl 4-(2,6-dimethyl-5-{[4-(trifluoromethyl)phenyl]ethynyl}pyrimidin-4-ylaminomethyl)benzoate, or
a pharmaceutically acceptable salt thereof;

(17) A pharmaceutical composition containing the compound or a pharmaceutically acceptable salt thereof according to any one of the above items (1) to (16);

(18) Use of the compound or a pharmaceutically acceptable salt thereof according to any one of the above items (1) to (16) in the manufacture of a medicament for use in the production of an anti-cell-proliferation effect in a warm-blooded animal;

(19) Use of the compound or a pharmaceutically acceptable salt according to any one of the above items (1) to (16) in the manufacture of a medicament for use in the production of an anticancer effect in a warm-blooded animal;

(20) Use of the compound or a pharmaceutically acceptable salt according to any one of the above items (1) to (16) in the manufacture of a medicament for use in the production of an anticancer effect during culture of warm-blooded animal cells;

(21) A medium containing the compound or a pharmaceutically acceptable salt thereof according to any one of the above items (1) to (16);

(22) Cells cultured in the medium containing the compound or a pharmaceutically acceptable salt thereof according to any one of the above items (1) to (16);

(23) Use of the compound or a pharmaceutically acceptable salt thereof according to any one of the above items (1) to (16) in the manufacture of a medicament for use in the production of a tyrosine kinase inhibitory effect in a warm-blooded animal;

(24) A pharmaceutical composition containing the compound, which may be a prodrug, or a pharmaceutically acceptable salt thereof according to any one of the above items (1) to (16);

(25) The pharmaceutical composition according to the above item (17) or (24) being a tyrosine kinase inhibitor;

(26) The pharmaceutical composition according to the above item (17) or (24) being an anticancer agent;

(27) An intermediate, which is the compound or a pharmaceutically acceptable salt thereof according to any one of the above items (1) to (16) and use thereof;

(28) An intermediate, which is the compound or a pharmaceutically acceptable salt thereof according to any one of the above items (1) to (16) for producing a tyrosine kinase inhibitor and use thereof;

(29) An intermediate, which is the compound or a pharmaceutically acceptable salt thereof according to any one of the above items (1) to (16) for producing an anticancer agent and use thereof;

(30) A method of producing an anti-cell-proliferation effect in a warm-blooded animal, comprising administering an effective amount of the compound or a pharmaceutically acceptable salt thereof according to any one of the above items (1) to (16) to the warm-blooded animal;

(31) A method of inhibiting tyrosine kinases comprising administering an effective amount of the compound or a pharmaceutically acceptable salt thereof according to any one of the above items (1) to (16) to a warm-blooded animal;

(32) A method of treating and/or preventing cancer, comprising administering an effective amount of the compound or a pharmaceutically acceptable salt thereof according to any one of the above items (1) to (16) to a warm-blooded animal; and

(33) A method of exerting an effect of inhibiting vascularization and/or an effect of reducing vascular permeability in a warm-blooded animal, comprising administering an effective amount of the compound or a pharmaceutically acceptable salt thereof according to any one of the above items (1) to (16) to the warm-blooded animal.

DESCRIPTION OF EMBODIMENTS

Terms and symbols used in the specification are defined below and the present invention will be more specifically described.

In the present invention, the terms "tumor" and "cancer" will be exchangeably used. Furthermore, in the present invention, tumor, malignant tumor, cancer, malignant neoplasm, carcinoma, sarcoma, and the like will be sometimes collectively referred to as "tumor" or "cancer".

In the specification, a generic term of an "alkyl group" includes both a linear alkyl group and a branched alkyl group. However, when individual alkyl groups such as a "propyl group" are referred to, a linear alkyl group alone is mentioned. The same definition is applied to other generic terms. Furthermore, in the specification, sec-, which is an abbreviation of "secondary", means a secondary carbon. Moreover, in the specification, tert-, which is an abbreviation of "tertiary", means a tertiary carbon.

Examples of a "halogen atom" include a fluorine atom, a chlorine atom, a bromine atom and an iodine atom.

The "$C_{1-6}$ alkyl group" refers to a monovalent group derived by removing a single hydrogen atom from a saturated aliphatic hydrocarbon having 1 to 6 carbon atoms, hence representing a linear or branched alkyl group having 1 to 6 carbon atoms. Examples thereof include a methyl group, an ethyl group, a propyl group, an isopropyl group, a butyl group, an isobutyl group, a sec-butyl group, a tert-butyl group, a pentyl group, an isopentyl group, a neopentyl group, a tert-pentyl group and a hexyl group, preferably include a methyl group, an ethyl group, an isopropyl group, an isobutyl group, an isopentyl group, a propyl group, a butyl group and a pentyl group, and further preferably include a methyl group and an ethyl group.

The "$C_{1-6}$ haloalkyl group" means that one or more hydrogen atoms of the above "$C_{1-6}$ alkyl group" may be replaced with one or more "halogen atoms" (i.e., a fluorine atom, a chlorine atom, a bromine atom and/or an iodine atom). As the "$C_{1-6}$ haloalkyl group", it is preferable that one or more hydrogen atoms of the above "$C_{1-6}$ alkyl group" are replaced with 1 to 6 or 1 to 3 fluorine atoms. Examples of the "$C_{1-6}$ haloalkyl group" include a trifluoromethyl group, a difluoromethyl group, a fluoromethyl group, a 1-chloroethyl group, a 1-fluoroethyl group, a 2-fluoroethyl group, a 1,1,2,2,2-pentafluoroethyl group, a 2,2,2-trifluoroethyl group, a 1,1,2,2-tetrafluoroethyl group, a 1,1,2,3,3,3-hexafluoropropyl group and a 3,3,3-trifluoropropyl group. Most preferably, a trifluoromethyl group is mentioned.

The "$C_{1-6}$ alkylene group" refers to a divalent group derived by removing two hydrogen atoms from a saturated aliphatic hydrocarbon having 1 to 6 carbon atoms, i.e., a linear or branched saturated divalent hydrocarbon group having 1 to 6 carbon atoms, that is, a linear or branched alkylene group having 1 to 6 carbon atoms. Examples thereof include a methylene group, an ethylene group, a methylmethylene group, an ethylmethylene group, a dimethylmethylene group, an ethylmethylmethylene group, an isopropylmethylene group, a trimethylene group, a propylene group, a 1-methyltrimethylene group, a 2-methyltrimethylene group, a tetramethylene group, a 1,1-dimethylethylene group, a 1,2-dimethylethylene group, a 1-ethylethylene group and a 2-ethylethylene group, preferably include a methylene group, a methylmethylene group, a dimethylmethylene group, an ethylene group and a trimethylene group, and more preferably include a methylene group.

The "$C_{3-8}$ cycloalkyl group" refers to a cycloalkyl group having 3 to 8 carbon atoms. Examples thereof include a cyclopropyl group, a cyclopentyl group and a cyclohexyl group.

The "$C_{3-6}$ cycloalkenyl group" refers to a cycloalkenyl group having 3 to 6 carbon atoms. Examples thereof include a 2-cyclopenten-1-yl group and a 2-cyclohexen-1-yl group.

The "$C_{4-6}$ cycloalkadienyl group" refers to a cycloalkadienyl group having 4 to 6 carbon atoms. Examples thereof include a 2,4-cyclopentadien-1-yl group, a 2,4-cyclohexadien-1-yl group and a 2,5-cyclohexadien-1-yl group.

The "$C_{2-6}$ alkenyl group" refers to a linear or branched alkenyl group having 2 to 6 carbon atoms and containing at least one double bond. Examples thereof include an allyl group, a 2-butenyl group, a 3-butenyl group, a 2-pentenyl group, a 3-pentenyl group, a 4-pentenyl group, a 2-hexenyl group, a 3-hexenyl group, a 4-hexenyl group, a 5-hexenyl group, a vinyl group and a 1-propenyl group.

The "$C_{2-6}$ alkynyl group" refers to a linear or branched alkynyl group having 2 to 6 carbon atoms and containing at least one triple bond. Examples thereof include a 2-propynyl group, a 2-butynyl group, a 3-butynyl group, a 2-pentynyl group, a 3-pentynyl group, a 4-pentynyl group, a 2-hexynyl group, a 3-hexynyl group, a 4-hexynyl group, a 5-hexynyl group and an ethynyl group.

The "$C_{1-6}$ alkoxy group" refers to a group obtained by covalently attaching the above "$C_{1-6}$ alkyl group" to an oxygen atom. Examples thereof include a methoxy group, an ethoxy group, a propoxy group, a butoxy group, an isopropoxy group, an isobutoxy group, a tert-butoxy group and a sec-butoxy group, and preferably include a methoxy group.

The "$C_{1-6}$ haloalkoxy group" means that one or more hydrogen atoms of the above "$C_{1-6}$ alkoxy group" may be replaced with one or more "halogen atoms" mentioned above (i.e., a fluorine atom, a chlorine atom, a bromine atom and/or an iodine atom). As the "$C_{1-6}$ haloalkoxy group", it is preferable that one or more hydrogen atoms of the above "$C_{1-6}$ alkoxy group" are replaced with 1 to 6 or 1 to 3 fluorine atoms. Examples of the "$C_{1-6}$ haloalkoxy group" include a 2,2,2-trifluoroethoxy group and a trifluoromethoxy group.

The "$C_{1-6}$ alkoxy $C_{1-6}$ alkyl group" refers to an alkoxyalkyl group having 2 to 12 carbon atoms, in which one or more hydrogen atoms of the above "$C_{1-6}$ alkyl group" may be replaced with the above "$C_{1-6}$ alkoxy group". Examples thereof include a methoxymethyl group, an ethoxymethyl group, a 1-butoxypropan-2-yl group, a 2-ethoxyethyl group, a 2-methoxyethyl group, a 1-ethoxyethyl group and a 1-methoxyethyl group.

The "$C_{1-6}$ alkylsulfanyl group" refers to a group obtained by covalently attaching the above "$C_{1-6}$ alkyl group" to a sulfur atom. Examples thereof include a methylsulfanyl group, an ethylsulfanyl group and a butylsulfanyl group.

The "$C_{1-6}$ alkylsulfinyl group" refers to a sulfinyl group having the above "$C_{1-6}$ alkyl group" covalently attached thereto. Examples thereof include a methylsulfinyl group, an ethylsulfinyl group and a butylsulfinyl group.

The "$C_{1-6}$ alkylsulfonyl group" refers to a sulfonyl group having the above "$C_{1-6}$ alkyl group" covalently attached thereto. Examples thereof include a methanesulfonyl group, an ethanesulfonyl group and a butanesulfonyl group.

The "$C_{1-6}$ alkoxycarbonyl group" refers to an alkoxycarbonyl group having 2 to 7 carbon atoms which is obtained by covalently attaching the above "$C_{1-6}$ alkoxy group" to a carbonyl group. Examples thereof include a methoxycarbonyl group, an ethoxycarbonyl group, a propoxycarbonyl group, an isopropoxycarbonyl group, a butoxycarbonyl group, an isobutoxycarbonyl group, a sec-butoxycarbonyl group, a tert-butoxycarbonyl group, a pentyloxycarbonyl group, an isopentyloxycarbonyl group and a neopentyloxycarbonyl group.

As the "aryl group" in the "aryl group which may have one or more substituents", a monocyclic, bicyclic or tricyclic aryl group having 6 to 14 carbon atoms is preferable. Examples of the "aryl group" include a phenyl group, a 1-naphthyl group and a 2-naphthyl group and preferably include a phenyl group.

Example of the "aryl group which may have one or more substituents" include a 4-chlorophenyl group, a 4-fluorophenyl group, a 4-(trifluoromethyl)phenyl group, a 2-chlorophenyl group, a 3-chlorophenyl group, a 2-fluorophenyl group, a 3-fluorophenyl group, a 4-methylphenyl group, a 2-methylphenyl group, a 3-methylphenyl group, a 2-(trifluoromethyl)phenyl group, a 3-(trifluoromethyl)phenyl group, a 2,3-dichlorophenyl group, a 3,4-dichlorophenyl group, a 2,4-dichlorophenyl group, a 2,5-dichlorophenyl group, a 2,6-dichlorophenyl group, a 3,5-dichlorophenyl group, a 2,3-difluorophenyl group, a 3,4-difluorophenyl group, a 2,4-difluorophenyl group, a 2,5-difluorophenyl group, a 2,6-difluorophenyl group, a 3,5-difluorophenyl group, a 2,4-bis (trifluoromethyl)phenyl group, a 2,5-bis(trifluoromethyl)phenyl group, a 2,6-bis(trifluoromethyl)phenyl group, a 3,5-bis(trifluoromethyl)phenyl group, a 4-chloro-3-fluorophenyl group, a 3-chloro-4-fluorophenyl group, a 2-chloro-4-fluorophenyl group, a 4-chloro-2-fluorophenyl group, a 3-fluoro-4-(trifluoromethyl)phenyl group, a 2-chloro-4-(trifluoromethyl)phenyl group, a 4-chloro-2-(trifluoromethyl)phenyl group, a 3-chloro-4-(trifluoromethyl)phenyl group, a 4-chloro-3-(trifluoromethyl)phenyl group, a 3,4-dimethoxyphenyl group, a 2,2-dimethyl-1,3-benzo[d]dioxol-4-yl group, a 2,2-difluoro-1,3-benzo[d]dioxol-4-yl group, a 1,3-benzo[d]dioxol-4-yl group, a 2,2-dimethyl-1,3-benzo[d]dioxol-5-yl group, a 2,2-difluoro-1,3-benzo[d]dioxol-5-yl group, a 1,3-benzo[d]dioxol-5-yl group, a 1,4-benzodioxan-5-yl group, a 1,4-benzodioxan-6-yl group, a 4-nitrophenyl group, a 3-nitrophenyl group, a 2-nitrophenyl group, a phenyl group, a 1-naphthyl group and a 2-naphthyl group.

As the "aralkyl group" in the "aralkyl group which may have one or more substituents", an aralkyl group having 7 to 15 carbon atoms is preferable. Examples of the "aralkyl group" include a benzyl group, a benzhydryl group, a phenethyl group, a naphthylmethyl group, a triphenylmethyl group and a cinnamyl group.

Examples of the "aralkyl group which may have one or more substituents" include a benzyl group, a benzhydryl group, a phenethyl group, naphthylmethyl group, a triphenylmethyl group, a cinnamyl group, a 4-methoxybenzyl group, a 2-nitrobenzyl group, a 4-nitrobenzyl group, a 3,4-dichlorobenzyl group, a 4-(trifluoromethyl)benzyl group and a 3-phthalidyl group.

The "aryl $C_{2-6}$ alkynyl group which may have one or more substituents" means that one or more hydrogen atoms of the above "$C_{2-6}$ alkynyl group" may be replaced with the above "aryl group which may have one or more substituents". Examples thereof include a [4-(trifluoromethyl)phenyl]ethynyl group, a (4-fluorophenyl)ethynyl group, a (4-chlorophenyl)ethynyl group, a [3-(trifluoromethyl)phenyl]ethynyl group, a [2-(trifluoromethyl)phenyl]ethynyl group, a (3-fluorophenyl)ethynyl group, a (2-fluorophenyl)ethynyl group, a (3-chlorophenyl)ethynyl group, a (2-chlorophenyl)ethynyl group, a (4-methylphenyl)ethynyl group, a (3-methylphenyl)ethynyl group, a (2-methylphenyl)ethynyl group, a (2,4-difluorophenyl)ethynyl group, a (3,5-difluorophenyl)ethynyl group, a (3,4-difluorophenyl)ethynyl group, a (4-fluoro-3-methylphenyl)ethynyl group, a [2,4-bis(trifluoromethyl)phenyl]ethynyl group, a [2,5-bis(trifluoromethyl)phenyl]ethynyl group, a [2,6-bis(trifluoromethyl)phenyl]ethynyl group, a [3,5-bis(trifluoromethyl)phenyl]ethynyl group, a (3,5-dimethylphenyl)ethynyl group, a (2,4-dimethylphenyl)ethynyl group, a (3-chloro-4-fluorophenyl)ethynyl group, a (2-chloro-4-fluorophenyl)ethynyl group, a (4-chloro-2-fluorophenyl)ethynyl group, a [4-chloro-2-(trifluoromethyl)phenyl]ethynyl group, a [2-chloro-4-(trifluoromethyl)phenyl] ethynyl group, a [4-chloro-3-(trifluoromethyl)phenyl] ethynyl group, a [3-fluoro-4-(trifluoromethoxy)phenyl] ethynyl group, a [4-(trifluoromethoxy)phenyl]ethynyl group, a (4-methoxyphenyl)ethynyl group, a (3,5-dimethoxyphenyl)ethynyl group, a (2,5-dimethoxyphenyl)ethynyl group, a (4-methoxy-2-methylphenyl)ethynyl group, a (2,4,5-trimethylphenyl)ethynyl group, a (2,4,6-trimethoxyphenyl)ethynyl group and a phenylethynyl group. Preferable examples thereof include a [4-(trifluoromethyl)phenyl]ethynyl group, a (4-fluorophenyl)ethynyl group, a (3-fluorophenyl)ethynyl group and a (4-methylphenyl)ethynyl group. More preferable examples thereof include a [4-(trifluoromethyl)phenyl]ethynyl group.

The "aryl $C_{2-6}$ alkenyl group which may have one or more substituents" means that one or more hydrogen atoms of the above "$C_{2-6}$ alkenyl group" may be replaced with the above "aryl group which may have one or more substituents". Examples thereof include a 2-[4-(trifluoromethyl)phenyl]vinyl group, a 2-(4-fluorophenyl)vinyl group, a 2-(4-chlorophenyl)vinyl group, a 2-phenylvinyl group, a 2-(4-methylphenyl)vinyl group, a 2-[3-(trifluoromethyl)phenyl]vinyl group, a 2-[2-(trifluoromethyl)phenyl]vinyl group, a 2-(3-fluorophenyl)vinyl group, a 2-(2-fluorophenyl)vinyl group, a 2-(3-chlorophenyl)vinyl group, a 2-(2-chlorophenyl)vinyl group, a 2-(3-methylphenyl)vinyl group, a 2-(2-methylphenyl)vinyl group, a 2-(2,4-difluorophenyl)vinyl group, a 2-(3,5-difluorophenyl)vinyl group, a 2-(3,4-difluorophenyl)vinyl group, a 2-(4-fluoro-3-methylphenyl)vinyl group, a 2-(3,5-dimethylphenyl)vinyl group, a 2-(2,5-dimethylphenyl)vinyl group, a 2-[2,4-bis(trifluoromethyl)phenyl]vinyl group, a 2-[2,5-bis(trifluoromethyl)phenyl]vinyl group, a 2-[2,6-bis(trifluoromethyl)phenyl]vinyl group, a 2-[3,5-bis(trifluoromethyl)phenyl]vinyl group, a 2-(3-chloro-4-fluorophenyl)vinyl group, a 2-(2-chloro-4-fluorophenyl)vinyl group, a 2-(4-chloro-2-fluorophenyl)vinyl group, a 2-[4-chloro-2-(trifluoromethyl)phenyl]vinyl group, a 2-[2-chloro-4-(trifluoromethyl)phenyl]vinyl group, a 2-[4-chloro-3-(trifluoromethyl)phenyl]vinyl group and a 2-(2,4,5-trimethylphenyl)vinyl group.

Examples of the "$C_{2-6}$ alkynyl group which may have one or more substituents" include a 3,3-dimethyl-1-butynyl group, a cyclopropylethynyl group, a cyclohexylethynyl group, a 3,3,3-trifluoropropynyl group, an ethynyl group, a 1-propynyl group, a 1-butynyl group, a 1-pentynyl group, a 1-hexynyl group, a 1-heptynyl group, a 1-octynyl group, a 1-decynyl group, a 3-methyl-1-butynyl group, a 3-cyclopentyl-1-propynyl group, a 3-cyclohexyl-1-propynyl group, a 3-hydroxy-1-propynyl group, a 5-hydroxy-1-pentynyl group, a 2-thienylethynyl group, a 3-thienylethynyl group, a 2-pyridylethynyl group, a 3-pyridylethynyl group, a 4-pyridylethynyl group, a 5-methoxycarbonyl-1-pentynyl group and a 5-ethoxycarbonyl-1-pentynyl group.

Examples of the "$C_{2-6}$ alkenyl group which may have one or more substituents" include a 3,3-dimethyl-1-butenyl group, a 2-(cyclopropyl)vinyl group, a 3,3,3-trifluoropropenyl group, a vinyl group, an isopropenyl group, a 2-(cyclohexyl)vinyl group, a 1-propenyl group, a 1-butenyl group, a 1-pentenyl group, a 1-hexenyl group, a 1-heptenyl group, a 1-octenyl group, a 1-decenyl group, a 3-methyl-1-butenyl group, a 3-methyl-2-butenyl group, a 3-cyclopentyl-1-propenyl group, a 3-cyclohexyl-1-propenyl group, a 2-(2-thienyl)vinyl group, a 2-(3-thienyl)vinyl group, a 2-(2-pyridyl)vinyl group, a 2-(3-pyridyl)vinyl group, a 2-(4-pyridyl)vinyl group, a 2-(methoxycarbonyl)vinyl group, a 2-(ethoxycarbonyl)vinyl group, a 2-carbamoylvinyl group, a 5-methoxycarbonyl-1-pentenyl group and a 5-ethoxycarbonyl-1-pentenyl group.

Examples of the "amino group which may have one or more substituents" include an amino group, a methylamino group, an ethylamino group, an isopropylamino group, a tert-butoxycarbonylamino group, an ethoxycarbonylamino group, an acetylamino group, a methanesulfonamide group, an N-methylmethanesulfonamide group, a trifluoromethanesulfonamide group, an N-methyltrifluoromethanesulfonamide group, a benzenesulfonamide group, an N,N-dimethylamino group, an N,N-diethylamino group, a 4-fluorobenzylamino group, an N-benzyl-N-methylamino group, an N-benzyl-N-phenylamino group and an N-phenylamino group.

The "amino $C_{1-6}$ alkyl group which may have one or more substituents" means that one or more hydrogen atoms of the above "$C_{1-6}$ alkyl group" may be replaced with the above "amino group which may have one or more substituents". Examples thereof include an N,N-dimethylaminomethyl group, an N,N-diethylaminomethyl group, a 2-(N,N-dimethylamino)ethyl group, a 2-(N,N-diethylamino)ethyl group, a 3-(N,N-dimethylamino)propyl group, a 3-(N,N-diethylamino)propyl group, a 4-(N,N-dimethylamino)butyl group and a 4-(N,N-diethylamino)butyl group. More preferable examples thereof include a 2-(N,N-diethylamino)ethyl group and a 2-(N,N-dimethylamino)ethyl group.

As the "heterocyclic ring" in the "heterocyclic group which may have one or more substituents", an aromatic or a non-aromatic 4- to 8-membered ring, which is composed of 1 to 4 hetero atoms independently selected from a nitrogen atom, an oxygen atom and/or a sulfur atom and a plurality of carbon atoms, is preferable. The "heterocyclic group" refers to a monovalent group derived by removing a single hydrogen atom from a heterocyclic ring. Examples of the "heterocyclic group" include a 2-thienyl group, a 3-thienyl group, a 2-pyridyl group, a 3-pyridyl group, a 4-pyridyl group, a 1,3-thiazol-2-yl group, a morpholino group, a piperidino group, a 1-pyrrolidinyl group, a piperidin-2-yl group, a piperidin-3-yl group, a piperidin-4-yl group, a piperazin-1-yl group, a homopiperazin-1-yl group, a homopiperidin-1-yl group, a pyrrolidin-2-yl group, a 3-quinuclidinyl group, an azetidin-3-yl group and a tetrahydrofuran-2-yl group.

Examples of the "heterocyclic group which may have one or more substituents" include a 2-thienyl group, a 3-thienyl group, a 5-methyl-2-thienyl group, a 2-pyridyl group, a 3-pyridyl group, a 4-pyridyl group, a 5-(trifluoromethyl)pyridin-2-yl group, a 3-(trifluoromethyl)pyridin-2-yl group, a 3,5-dichloropyridin-2-yl group, a 1,3-thiazol-2-yl group, a 5-methyl-1,3-thiazol-2-yl group, a 4-methyl-1,3-thiazol-2-yl group, a morpholino group, a piperidino group, a 1-pyrrolidinyl group, a piperidin-3-yl group, a piperidin-4-yl group, a piperazin-1-yl group, a homopiperazin-1-yl group, a homopiperidin-1-yl group, a pyrrolidin-2-yl group, a 3-quinuclidinyl group, an N-methylpiperidin-4-yl group, an N-ethylpiperidin-4-yl group, an N-propylpiperidin-4-yl group, an N-butylpiperidin-4-yl group, an N-methylpiperidin-3-yl group, an N-ethylpiperidin-3-yl group, an N-propylpiperidin-3-yl group, an N-butylpiperidin-3-yl group, an N-benzylpiperidin-4-yl group, an N-benzylpiperidin-3-yl group, an N-methylpyrrolidin-3-yl group, an N-ethylpyrrolidin-3-yl group, an N-methylpiperidin-2-yl group, an N-ethylpiperidin-2-yl group, an N-propylpiperidin-2-yl group, an N-butylpiperidin-2-yl group, a pyrrolidin-3-yl group, an N-methylpyrrolidin-2-yl group, an N-ethylpyrrolidin-2-yl group, a 4-diphenylmethylpiperazin-1-yl group, an N-diphenylmethylpiperidin-4-yl group, an N-diphenylmethylazetidin-3-yl group, an N-benzylpyrrolidin-3-yl group, an 8-methyl-8-azabicyclo[3.2.1]octan-3-yl group and a 9-methyl-9-azabicyclo[3.3.1]nonan-3-yl group.

The "heterocyclic $C_{1-6}$ alkyl group which may have one or more substituents" means that one or more hydrogen atoms of the above "$C_{1-6}$ alkyl group" may be replaced with the above "heterocyclic group which may have one or more substituents". Examples thereof include a morpholinomethyl group, a 2-morpholinoethyl group, a 3-morpholinopropyl group, a 4-morpholinobutyl group, a piperidinomethyl group, a 2-piperidinoethyl group, a 3-piperidinopropyl group, a 4-piperidinobutyl group, a pyrrolidin-1-ylmethyl group, a 2-(pyrrolidin-1-yl)ethyl group, a 3-(pyrrolidin-1-yl)propyl group, a 4-(pyrrolidin-1-yl)butyl group, a 2-(4-methylpiperazin-1-yl)ethyl group, a 3-(4-methylpiperazin-1-yl)propyl group, a 4-(4-methylpiperazin-1-yl)butyl group, a 4-methylpiperazin-1-ylmethyl group, a 2-(4-ethylpiperazin-1-yl)ethyl group, a 3-(4-ethylpiperazin-1-yl)propyl group, a 4-(4-ethylpiperazin-1-yl)butyl group, a 4-ethylpiperazin-1-ylmethyl group, a piperazin-1-ylmethyl group, a 2-(piperazin-1-yl)ethyl group, a 3-(piperazin-1-yl)propyl group, a 4-(piperazin-1-yl)butyl group, an N-ethylpiperidin-3-ylmethyl group, a 2-(N-methylpiperidin-3-yl)ethyl group, a 3-(N-methylpiperidin-3-yl)propyl group, a 4-(N-methylpiperidin-3-yl)butyl group, a 2-(N-ethylpiperidin-3-yl)ethyl group, a 3-(N-ethylpiperidin-3-yl)propyl group, a 4-(N-ethylpiperidin-3-yl)butyl group, an N-methylpiperidin-4-ylmethyl group, a 2-(N-methylpiperidin-4-yl)ethyl group, a 3-(N-methylpiperidin-4-yl)propyl group, a 4-(N-methylpiperidin-4-yl)butyl group, an N-ethylpiperidin-4-ylmethyl group, a 2-(N-ethylpiperidin-4-yl)ethyl group, a 3-(N-ethylpiperidin-4-yl)propyl group, a 4-(N-ethylpiperidin-4-yl)butyl group, an N-methylpiperidin- group, a 2-(N-methylpiperidin-2-yl)ethyl group, a 3-(N-methylpiperidin-2-yl)propyl group, a 4-(N-methylpiperidin-2-yl)butyl group, an N-ethylpiperidin-2-ylmethyl group, a 2-(N-ethylpiperidin-2-yl)ethyl group, a 3-(N-ethylpiperidin-2-yl)propyl group, a 4-(N-ethylpiperidin-2-yl)butyl group, a piperidin-2-ylmethyl group, a piperidin-3-ylmethyl group, a piperidin-4-ylmethyl group, a 2-(piperidin-3-yl)ethyl group, a 2-(piperidin-4-yl)ethyl group, a 3-(piperidin-3-yl)propyl group, a 3-(piperidin-4-yl)propyl group, a 4-(piperidin-3-yl)butyl group, a 4-(piperidin-4-yl)butyl group, a 2-(homopiperidin-1-yl)ethyl group, a 3-(homopiperidin-1-yl)propyl group, a 2-(homopiperazin-1-yl)ethyl group, a 3-(homopiperazin-1-yl)propyl group, a 2-(N-methylpyrrolidin-3-yl)ethyl group, a 3-(N-methylpyrrolidin-3-yl)propyl group, a 4-(N-methylpyrrolidin-3-yl)butyl group, an N-methylpyrrolidin-3-ylmethyl group, a 2-(N-ethylpyrrolidin-3-yl)ethyl group, a 3-(N-ethylpyrrolidin-3-yl)propyl group, a 4-(N-ethylpyrrolidin-3-yl)butyl group, an N-ethylpyrrolidin-3-ylmethyl group, a 2-(pyrrolidin-3-yl)ethyl group, a 3-(pyrrolidin-3-yl)propyl group, a 4-(pyrrolidin-3-yl)butyl group, a pyrrolidin-3-ylmethyl group, a 2-(N-methylpyrrolidin-2-yl)ethyl group, a 3-(N-methylpyrrolidin-2-yl)propyl group, a 4-(N-methylpyrrolidin-2-yl)butyl group, an N-methylpyrrolidin-2-ylmethyl group, a 2-(N-ethylpyrrolidin-2-yl)ethyl group, a 3-(N-ethylpyrrolidin-2-yl)propyl group, a 4-(N-ethylpyrrolidin-2-yl)butyl group, an N-ethylpyrrolidin-2-ylmethyl group, a 2-(pyrrolidin-2-yl)ethyl group, a 3-(pyrrolidin-2-yl)propyl group, a 4-(pyrrolidin-2-yl)butyl group and a pyrrolidin-2-ylmethyl group. Preferable examples thereof include a 2-morpholinoethyl group, a 2-piperidinoethyl group, a tetrahydrofuran-2-ylmethyl, 2-(tetrahydrofuran-2-yl)ethyl group and a 3-(tetrahydrofuran-2-yl)propyl group.

In the "aryl group which may have one or more substituents", "aralkyl group which may have one or more substituents", "heterocyclic group which may have one or more substituents", "an aryl $C_{2-6}$ alkynyl group which may have one or more substituents" and "aryl $C_{2-6}$ alkenyl group which may have one or more substituents", the substituent is a substituent selected from the following $T^1$ group but not particularly limited thereto. Preferably, a halogen atom, a $C_{1-6}$ haloalkyl group or a $C_{1-6}$ alkyl group is mentioned. These substituents (0, 1 or more, preferably 0 to 5, further preferably 1 to 3) may be present at replaceable positions.

$T^1$ group; a halogen atom, a $C_{1-6}$ alkyl group, a $C_{1-6}$ haloalkyl group, a $C_{3-8}$ cycloalkyl group, a $C_{3-8}$ halocycloalkyl group (e.g., a 2-fluorocyclopropyl group), a $C_{2-6}$ alkenyl group, a $C_{2-6}$ alkynyl group, a $C_{1-6}$ alkoxy group, a dimethylmethylenedioxy group, a difluoromethylenedioxy group, a methylenedioxy group, an ethylenedioxy group, a $C_{1-6}$ haloalkoxy group, a $C_{1-6}$ alkoxy $C_{1-6}$ alkyl group, a $C_{1-6}$ alkylsulfanyl group, a hydroxy group, a $C_{1-6}$ alkoxycarbonyl group, a carboxyl group, an acyl group (e.g., a formyl group, a benzoyl group, an acetyl group), a nitro group, a cyano group, a sulfamoyl group, a $C_{1-6}$ alkylsulfonyl group, a sulfanyl group, an amino group, a methylamino group, an ethylamino group, an isopropylamino group, a tert-butoxycarbonylamino group, an ethoxycarbonylamino group, an acetylamino group, a methanesulfonamide group, an N-methylmethanesulfonamide group, a trifluoromethanesulfonamide group, an N-methyltrifluoromethanesulfonamide group, a benzenesulfonamide group, an N,N-dimethylamino group, an N,N-diethylamino group, a 4-fluorobenzylamino group, an N-benzyl-N-methylamino group, an N-benzyl-N-phenylamino group, an N-phenylamino group, a carbamoyl group, a $C_{3-6}$ cycloalkenyl group and a $C_{4-6}$ cycloalkadienyl group.

In "a $C_{2-6}$ alkynyl group which may have one or more substituents" and "a $C_{2-6}$ alkenyl group which may have one or more substituents", the substituent is a substituent selected from the following $T^2$ group but not particularly limited thereto. Preferably a heterocyclic group which may have one or more substituents, a $C_{1-6}$ alkyl group, a $C_{3-8}$ cycloalkyl group, a $C_{1-6}$ haloalkyl group, a $C_{1-6}$ alkoxy group, a carbamoyl group or a $C_{1-6}$ alkoxycarbonyl group is mentioned. These substituents (0 to 3, preferably 0 to 1) may be present at replaceable positions.

$T^2$ group; a heterocyclic group which may have one or more substituents, a halogen atom, a $C_{1-6}$ alkyl group, a $C_{1-6}$ haloalkyl group, a $C_{1-6}$ alkoxy $C_{1-6}$ alkyl group, a $C_{3-8}$ cycloalkyl group, a $C_{3-8}$ halocycloalkyl group (e.g., a 2-fluorocyclopropyl group), a $C_{2-6}$ alkenyl group, a $C_{2-6}$ alkynyl group, a $C_{1-6}$ alkoxy group, a $C_{1-6}$ haloalkoxy group, a hydroxyl group, a $C_{1-6}$ alkoxycarbonyl group, a carboxyl group, an acyl group (e.g., a formyl group, a benzoyl group, an acetyl group), a silyl group derivative (e.g., a trimethylsilyl group, a triethylsilyl group, a biphenyldiethylsilyl group), a carbamoyl group, a $C_{3-6}$ cycloalkenyl group and a $C_{4-6}$ cycloalkadienyl group.

In the "amino group which may have one or more substituents", the substituent is a substituent selected from the following $T^3$ group but not particularly limited thereto. These substituents (0 to 2) may be present at replaceable positions.

$T^3$ group; a $C_{1-6}$ alkyl group, an aralkyl group which may have one or more substituents, an aryl group which may have one or more substituents, a $C_{1-6}$ alkoxy $C_{1-6}$ alkyl group, a $C_{3-8}$ cycloalkyl group, a $C_{3-8}$ halocycloalkyl group (e.g., a 2-fluorocyclopropyl group), a $C_{1-6}$ haloalkyl group, a $C_{2-6}$ alkenyl group, an aryl $C_{2-6}$ alkenyl group which may have one or more substituents, a $C_{1-6}$ alkoxycarbonyl group, an acyl group (e.g., a formyl group, a benzoyl group, an acetyl group), a carboxyl group, a $C_{1-6}$ alkylsulfonyl group, a $C_{1-6}$ haloalkylsulfonyl group (e.g., a trifluoromethanesulfonyl group), an arylsulfonyl group which may have one or more substituents (e.g., a benzenesulfonyl group), a $C_{3-6}$ cycloalkenyl group and a $C_{4-6}$ cycloalkadienyl group.

Next, $R^1$, $R^2$, $R^3$, $R^4$, $R^5$, $R^6$, $R^7$ and X in the general formula (1) to the general formula (7) of a compound of the present invention or a pharmaceutically acceptable salt thereof (a heterocyclic compound of the present invention) will be exemplified and a compound of the present invention or a pharmaceutically acceptable salt thereof will be more specifically described below. Note that the ranges of the general formula (1) to the general formula (7) are not limited by these specific examples.

Examples of $R^1$ described in the general formula (1) to the general formula (7) include a hydrogen atom, a methyl group, an ethyl group, an isopropyl group, an isobutyl group, an isopentyl group, a propyl group, a butyl group and a pentyl group. Preferably examples thereof include a methyl group and an ethyl group. Furthermore, $R^1$ may be a protecting group of a carboxyl group. Examples of the protecting group used for protecting a carboxyl group include the protecting groups described in JOHN WILEY & SONS, "GREENE'S PROTECTIVE GROUPS IN ORGANIC SYNTHESIS (FOURTH EDITION)" written by T. Greene et al., pp. 533-646.

Examples of $R^2$ described in the general formula (1) to the general formula (7) include a hydrogen atom, a methyl group, an ethyl group, an isopropyl group, a trifluoromethyl group and a fluorine atom. Preferable examples thereof include a methyl group and an ethyl group. More Preferable examples thereof include a methyl group.

Alternatively, $R^2$ described in the general formula (1) or the general formula (2) and a carbon atom covalently attached to $R^2$, i.e., a C—$R^2$, may be replaced with a nitrogen atom.

Examples of $R^3$ in the general formula (1) include a trifluoromethyl group, a 1-propynyl group, a 3,3,3-trifluoro-1-propynyl group, an ethynyl group, a (3-chlorophenyl)ethynyl group, a (4-fluorophenyl)ethynyl group and a [4-(trifluoromethyl)phenyl]ethynyl group. Preferable examples thereof include an ethynyl group, a (4-fluorophenyl)ethynyl group and a [4-(trifluoromethyl)phenyl]ethynyl group. More Preferable examples thereof include a [4-(trifluoromethyl)phenyl]ethynyl group. Furthermore, as $R^3$ of the general formula (1), an electron-withdrawing group (a group having an electron-withdrawing property, a group having a hyperconjugative effect, etc.) and/or a group having π-orbital are rather preferable.

Examples of $R^3$ described in the general formula (2) and the general formula (3) include a fluorine atom, a chlorine atom, a trifluoromethyl group, a phenyl group, a 1-propynyl group, a 3,3,3-trifluoro-1-propynyl group, an ethynyl group, a (3-chlorophenyl)ethynyl group, a (4-chlorophenyl)ethynyl group, a (4-fluorophenyl)ethynyl group and a [4-(trifluoromethyl)phenyl]ethynyl group. Preferable examples thereof include an ethynyl group, a (4-fluorophenyl)ethynyl group and a [4-(trifluoromethyl)phenyl]ethynyl group. More preferable examples thereof include a [4-(trifluoromethyl)phenyl]ethynyl group. Furthermore, as examples of $R^3$ described in the general formula (2) and the general formula (3), each independently, an electron-withdrawing group (a group having an electron-withdrawing property, a group having a hyperconjugative effect, etc.) and/or a group having a π orbital are rather preferable.

As examples of $R^3$ described in the general formula (4) and the general formula (5), each independently, a fluorine atom, a chlorine atom, a trifluoromethyl group and a methyl group are mentioned. Preferable examples thereof include a fluorine atom, a chlorine atom and a trifluoromethyl group. More preferable examples thereof include a trifluoromethyl group. Furthermore, as examples of $R^3$ described in the general formula (4) and the general formula (5), each independently, an electron-withdrawing group (a group having an electron-withdrawing property, a group having a hyperconjugative effect, etc.) is preferable.

Examples of $R^3$ of the general formula (6) include a hydrogen atom, a fluorine atom, a chlorine atom, a trifluoromethyl group and a methyl group. Preferable examples thereof include a fluorine atom, a chlorine atom and a trifluoromethyl group. More preferable examples include a trifluoromethyl group. Furthermore, as $R^3$ of the general formula (6), an electron-withdrawing group (a group having an electron-withdrawing property, a group having a hyperconjugative effect, etc.) is preferable.

Alternatively, a bicyclic fused ring may be formed by sharing two carbon atoms, to which $R^2$ and $R^3$ described in the general formula (1) to the general formula (3) respectively bind, with a saturated or an unsaturated 5-membered ring or 6-membered ring (including e.g., a benzene ring, a thiophene ring, a furan ring and a cyclohexane ring) which may have one or more substituents (examples of the substituent, which is not particularly limited, include a halogen atom (e.g., a chlorine atom, a fluorine atom), a $C_{1-6}$ alkyl group (e.g., a methyl group), a $C_{1-6}$ alkoxy group (e.g., a methoxy group or a 2-methoxyethyloxy group), and a heterocyclic $C_{1-6}$ alkyl group which may have one or more —O-substituents (e.g., a 3-morpholinopropyloxy group), while the number of substituents present at replaceable positions is not limited).

Examples of $R^4$ described in the general formula (1), the general formula (2) and the general formula (4) include a hydrogen atom, a methyl group, an ethyl group and an isopropyl group. Preferable examples thereof include a hydrogen atom. Furthermore, $R^4$ may be a protecting group of an amino group. Examples of the protecting group used for protecting an amino group include the protecting groups described in JOHN WILEY & SONS, "GREENE'S PROTECTIVE GROUPS IN ORGANIC SYNTHESIS (FOURTH EDITION)" written by T. Greene et al., pp. 696-926.

Examples of $R^5$ described in the general formula (1), the general formula (2) and the general formula (4) include a hydrogen atom, a methyl group, an isopropyl group, a cyclopropyl group and a fluorine atom.

Alternatively, $R^5$ of the general formula (1) or the general formula (2) and a carbon atom covalently attached to $R^5$, i.e., a C—$R^5$, may be replaced with a nitrogen atom.

Examples of $R^6$ described in the general formula (1) each independently include a fluorine atom, a chlorine atom, a methoxy group, an ethoxy group, a propoxy group, a butoxy group, an isopropoxy group, an isobutoxy group, a tert-butoxy group, a sec-butoxy group and an ethynyl group. Preferable examples thereof include a fluorine atom, a chlorine atom and a methoxy group.

Examples of X described in the general formula (1), the general formula (2) and the general formula (4) include a methylene group, a methylmethylene group and a dimethylmethylene group. Preferable examples thereof include a methylene group.

Of the compounds of the present invention, a preferable compound is at least one compound selected from the group consisting of methyl 5-(6-methyl-5-{[4-(trifluoromethyl)phenyl]ethynyl}pyrimidin-4-ylaminomethyl)-2-furancarboxylate, ethyl 5-(6-methyl-5-{[4-(trifluoromethyl)phenyl]ethynyl}pyrimidin-4-ylaminomethyl)-2-furancarboxylate, isopropyl 5-(6-methyl-5-{[4-(trifluoromethyl)phenyl]ethynyl}pyrimidin-4-ylaminomethyl)-2-furancarboxylate, isobutyl 5-(6-methyl-5-{[4-(trifluoromethyl)phenyl]ethynyl}pyrimidin-4-ylaminomethyl)-2-furancarboxylate, isopentyl 5-(6-methyl-5-{[4-(trifluoromethyl)phenyl]ethynyl}pyrimidin-4-ylaminomethyl)-2-furancarboxylate, propyl 5-(6-methyl-5-{[4-(trifluoromethyl)phenyl]ethynyl}pyrimidin-4-ylaminomethyl)-2-furancarboxylate, butyl 5-(6-methyl-5-{[4-(trifluoromethyl)phenyl]ethynyl}pyrimidin-4-ylaminomethyl)-2-furancarboxylate, methyl 5-(6-ethyl-5-{[4-(trifluoromethyl)phenyl]ethynyl}pyrimidin-4-ylaminomethyl)-2-furancarboxylate, ethyl 5-(6-ethyl-5-{[4-(trifluoromethyl)phenyl]ethynyl}pyrimidin-4-ylaminomethyl)-2-furancarboxylate, methyl 4-(6-methyl-5-{[4-(trifluoromethyl)phenyl]ethynyl}pyrimidin-4-ylaminomethyl)benzoate, ethyl 4-(6-methyl-5-{[4-(trifluoromethyl)phenyl]ethynyl}pyrimidin-4-ylaminomethyl)benzoate, methyl 4-(6-ethyl-5-{[4-(trifluoromethyl)phenyl]ethynyl}pyrimidin-4-ylaminomethyl)benzoate, ethyl 4-(6-ethyl-5-{[4-(trifluoromethyl)phenyl]ethynyl}pyrimidin-4-ylaminomethyl)benzoate, methyl 5-(5-{[4-(trifluoromethyl)phenyl]ethynyl}pyrimidin-4-ylaminomethyl)-2-furancarboxylate, ethyl 5-(5-{[4-(trifluoromethyl)phenyl]ethynyl}pyrimidin-4-ylaminomethyl)-2-furancarboxylate, methyl 4-(5-{[4-(trifluoromethyl)phenyl]ethynyl}pyrimidin-4-ylaminomethyl)benzoate, ethyl 4-(5-{[4-(trifluoromethyl)phenyl]ethynyl}pyrimidin-4-ylaminomethyl)benzoate, methyl 5-(2,6-dimethyl-5-{[4-(trifluoromethyl)phenyl]ethynyl}pyrimidin-4-ylaminomethyl)-2-furancarboxylate, ethyl 5-(2,6-dimethyl-5-{[4-(trifluoromethyl)phenyl]ethynyl}pyrimidin-4-ylaminomethyl)-2-furancarboxylate, methyl 4-(2,6-dimethyl-5-{[4-(trifluoromethyl)phenyl]ethynyl}pyrimidin-4-ylaminomethyl)benzoate, ethyl 4-(2,6-dimethyl-5-{[4-(trifluoromethyl)phenyl]ethynyl}pyrimidin-4-ylaminomethyl)benzoate, methyl 5-(2-isopropyl-6-methyl-5-{[4-(trifluoromethyl)phenyl]ethynyl}pyrimidin-4-ylaminomethyl)-2-furancarboxylate, ethyl 5-(2-isopropyl-6-methyl-5-{[4-(trifluoromethyl)phenyl]ethynyl}pyrimidin-4-ylaminomethyl)-2-furancarboxylate, methyl 4-(2-isopropyl-6-methyl-5-{[4-(trifluoromethyl)phenyl]ethynyl}pyrimidin-4-ylaminomethyl)benzoate and ethyl 4-(2-isopropyl-6-methyl-5-{[4-(trifluoromethyl)phenyl]ethynyl}pyrimidin-4-ylaminomethyl)benzoate or a pharmaceutically acceptable salt thereof.

Of the compounds of the present invention, a preferable compound is at least one compound selected from the group consisting of methyl 5-(6-methyl-5-{[4-(trifluoromethyl)phenyl]ethynyl}pyrimidin-4-ylaminomethyl)-2-furancarboxylate, ethyl 5-(6-methyl-5-{[4-(trifluoromethyl)phenyl]ethynyl}pyrimidin-4-ylaminomethyl)-2-furancarboxylate, methyl 4-(6-methyl-5-{[4-(trifluoromethyl)phenyl]ethynyl}pyrimidin-4-ylaminomethyl)benzoate, ethyl 4-(6-methyl-5-{[4-(trifluoromethyl)phenyl]ethynyl}pyrimidin-4-ylaminomethyl)benzoate, methyl 5-(2,6-dimethyl-5-{[4-(trifluoromethyl)phenyl]ethynyl}pyrimidin-4-ylaminomethyl)-2-furancarboxylate, ethyl 5-(2,6-dimethyl-5-{[4-(trifluoromethyl)phenyl]ethynyl}pyrimidin-4-ylaminomethyl)-2-furancarboxylate, methyl 4-(2,6-dimethyl-5-{[4-(trifluoromethyl)phenyl]ethynyl}pyrimidin-4-ylaminomethyl)benzoate, ethyl 4-(2,6-dimethyl-5-{[4-(trifluoromethyl)phenyl]ethynyl}pyrimidin-4-ylaminomethyl)benzoate, methyl 5-(2-isopropyl-6-methyl-5-{[4-(trifluoromethyl)phenyl]ethynyl}pyrimidin-4-ylaminomethyl)-2-furancarboxylate, ethyl 5-(2-isopropyl-6-methyl-5-{[4-(trifluoromethyl)phenyl]ethynyl}pyrimidin-4-ylaminomethyl)-2-furancarboxylate, methyl 4-(2-isopropyl-6-methyl-5-{[4-(trifluoromethyl)phenyl]ethynyl}pyrimidin-4-ylaminomethyl)benzoate and ethyl 4-(2-isopropyl-6-methyl-5-{[4-(trifluoromethyl)phenyl]ethynyl}pyrimidin-4-ylaminomethyl)benzoate or a pharmaceutically acceptable salt thereof.

Of the compounds of the present invention, a more preferable compound is at least one compound selected from the group consisting of methyl 5-(2,6-dimethyl-5-{[4-(trifluoromethyl)phenyl]ethynyl}pyrimidin-4-ylaminomethyl)-2-furancarboxylate, ethyl 5-(2,6-dimethyl-5-{[4-(trifluoromethyl)phenyl]ethynyl}pyrimidin-4-ylaminomethyl)-2-furancarboxylate, methyl 5-(2-isopropyl-6-methyl-5-{[4-(trifluoromethyl)phenyl]ethynyl}pyrimidin-4-ylaminomethyl)-2-furancarboxylate, ethyl 5-(2-isopropyl-6-methyl-5-{[4-(trifluoromethyl)phenyl]ethynyl}pyrimidin-4-ylaminomethyl)-2-furancarboxylate, methyl 5-(6-methyl-5-

{[4-(trifluoromethyl)phenyl]ethynyl}pyrimidin-4-ylaminomethyl)-2-furancarboxylate and ethyl 5-(6-methyl-5-{[4-(trifluoromethyl)phenyl]ethynyl}pyrimidin-4-ylaminomethyl)-2-furancarboxylate or a pharmaceutically acceptable salt thereof.

Of the compounds of the present invention, a most preferable compound is at least one compound selected from the group consisting of methyl 5-(6-methyl-5-{[4-(trifluoromethyl)phenyl]ethynyl}pyrimidin-4-ylaminomethyl)-2-furancarboxylate and ethyl 5-(6-methyl-5-{[4-(trifluoromethyl)phenyl]ethynyl}pyrimidin-4-ylaminomethyl)-2-furancarboxylate or a pharmaceutically acceptable salt thereof.

Examples of the compounds of the present invention also include 5-(pyrimidin-4-ylaminomethyl)-2-furancarboxylate derivative or a pharmaceutically acceptable salt thereof, 5-(pyrimidin-4-ylamino-1-ethyl)-2-furancarboxylate derivative or a pharmaceutically acceptable salt thereof, 5-(pyrimidin-4-ylamino-2-ethyl)-2-furancarboxylate derivative or a pharmaceutically acceptable salt thereof and 4-(pyrimidin-4-ylaminomethyl)benzoate derivative or a pharmaceutically acceptable salt thereof.

Hereinafter, as specific examples of a pharmaceutical composition, a medicament and/or an intermediate of the present invention, Table 1 to Table 3 show the structure of the compounds of the present invention. These are easily synthesized by the method described below, the methods described in Examples, the method well known to those skilled in the art of organic chemistry or modified methods of these. However, the present invention is not limited to the following compounds. In the tables, the following abbreviation is used. No.: Compound number (produced in Examples).

TABLE 1

| No. | R$^1$ | R$^2$ | R$^3$ |
|---|---|---|---|
| 1 | Ethyl | Methyl | Trifluoromethyl |
| 2 | Methyl | Methyl | Trifluoromethyl |
| 3 | Isopropyl | Methyl | Trifluoromethyl |
| 4 | Isobutyl | Methyl | Trifluoromethyl |
| 5 | Isopentyl | Methyl | Trifluoromethyl |
| 6 | Propyl | Methyl | Trifluoromethyl |
| 7 | Butyl | Methyl | Trifluoromethyl |
| 8 | Pentyl | Methyl | Trifluoromethyl |
| 9 | Ethyl | Ethyl | Trifluoromethyl |
| 10 | Methyl | Ethyl | Trifluoromethyl |
| 11 | Isopropyl | Ethyl | Trifluoromethyl |
| 12 | Isobutyl | Ethyl | Trifluoromethyl |
| 13 | Isopentyl | Ethyl | Trifluoromethyl |

TABLE 2

| No. | R$^1$ | R$^2$ | R$^3$ |
|---|---|---|---|
| 14 | Propyl | Ethyl | Trifluoromethyl |
| 15 | Butyl | Ethyl | Trifluoromethyl |
| 16 | Pentyl | Ethyl | Trifluoromethyl |
| 17 | Ethyl | Isopropyl | Trifluoromethyl |
| 18 | Methyl | Isopropyl | Trifluoromethyl |
| 19 | Ethyl | Isopropyl | Fluorine |
| 20 | Methyl | Isopropyl | Fluorine |
| 21 | Ethyl | Methyl | Fluorine |
| 22 | Methyl | Methyl | Fluorine |
| 23 | Ethyl | Methyl | Methyl |
| 24 | Methyl | Methyl | Methyl |
| 25 | Ethyl | Methyl | Hydrogen |
| 26 | Methyl | Methyl | Hydrogen |

TABLE 3

| No. | R$^1$ | R$^2$ | R$^3$ |
|---|---|---|---|
| 27 | Ethyl | Methyl | Trifluoromethyl |
| 28 | Methyl | Methyl | Trifluoromethyl |
| 29 | Isopropyl | Methyl | Trifluoromethyl |
| 30 | Isobutyl | Methyl | Trifluoromethyl |
| 31 | Isopentyl | Methyl | Trifluoromethyl |
| 32 | Propyl | Methyl | Trifluoromethyl |
| 33 | Butyl | Methyl | Trifluoromethyl |
| 34 | Pentyl | Methyl | Trifluoromethyl |
| 35 | Ethyl | Ethyl | Trifluoromethyl |
| 36 | Methyl | Ethyl | Trifluoromethyl |
| 37 | Isopropyl | Ethyl | Trifluoromethyl |
| 38 | Isobutyl | Ethyl | Trifluoromethyl |
| 39 | Isopentyl | Ethyl | Trifluoromethyl |

A compound of the present invention or a pharmaceutically acceptable salt thereof may have one or more isomers (e.g., optical isomers, geometric isomers and tautomers). The present invention includes these isomers as individual forms or as mixtures thereof. Furthermore, a compound of the present invention or a pharmaceutically acceptable salt thereof may have one or more asymmetric carbon atoms and an optical isomer based on the asymmetric carbon atom. Both the cases where these optical isomers are used individually and as a mixture of optical isomers are included in the present invention.

Furthermore, the present invention includes a prodrug of a compound of the present invention or a pharmaceutically acceptable salt thereof. The "prodrug" means a compound having a group, which is known to those skilled in the art of a medicament technology and organic chemistry, converted into a carboxyl group, an amino group, a hydroxy group, etc., through e.g., hydrolysis, oxidation, reduction and/or decarboxylation by reaction with an enzyme and/or a non-enzymatic substance (e.g., gastric acid) in vivo under physiological conditions. The "prodrug" may possibly have a preferable effect upon properties (pharmacological properties and/or pharmacokinetic properties) of a compound in a living body such as solubility, absorbability, stability, duration of action, activity in one or more target tissues, biodistribution, metabolism and excretion, toxicity, side effect, taste and odor.

Furthermore, a compound of the present invention may sometimes form an acid addition salt or a base potentially forming such a salt (i.e., a free base). As a salt of a compound of the present invention, a pharmaceutically acceptable salt is preferable. For example, a salt with an inorganic base, a salt with an organic base, a salt with an inorganic acid, a salt with an organic acid and a salt with a basic or acidic amino acid are used. Examples of the salt with an inorganic base include alkali metal salts such as a sodium salt and a potassium salt, alkaline-earth metal salts such as a calcium salt and a magnesium salt, an aluminum salt and an ammonium salt. Examples of the salt with an organic base include salts with trimethylamine, triethylamine, pyridine, picoline, ethanolamine, diethanolamine, triethanolamine, dicyclohexylamine, N,N'-dibenzylethylenediamine, methylamine, ethylamine, dimethylamine and diethylamine. Examples of the salt with an inorganic acid include salts with hydrochloric acid, hydrobromic acid, hydroiodic acid, nitric acid, sulfuric acid and phosphoric acid. Examples of the salt with an organic acid include salts with formic acid, acetic acid, trifluoroacetic acid, fumaric acid, oxalic acid, tartaric acid, maleic acid, citric acid, succinic acid, malic acid, propionic acid, malonic acid, lactic acid, methanesulfonic acid, ethanesulfonic acid, benzenesulfonic acid, p-toluenesulfonic acid, naphthalene sulfonic acid, glycolic acid, benzoic acid, cinnamic acid, mandelic acid, salicylic acid, gluconic acid, and saccharic acid (including aldaric acid, glucosaccharic acid, (glucaric acid, gular acid)). Examples of the salt with a basic amino acid include salts with arginine, lysine and ornithine. Examples of the salt with acidic amino acid include salts with aspartic acid and glutamic acid.

Furthermore, the present invention includes various types of hydrates and solvates as well as crystalline forms of a compound of the present invention or a pharmaceutically acceptable salt thereof. Furthermore, the present invention includes compounds labeled with various types of radioactive or nonradioactive isotopes.

{General Production Method}

A compound of the present invention and a pharmaceutically acceptable salt thereof can be produced by applying various known synthesis methods utilizing properties of substituents based on their structures or types. At this time, depending upon the type of functional group, it is sometimes effective, in view of production technique, to block the functional group with an appropriate protecting group, in other words, using a group easily converting into the desired functional group instead of using the functional group as it is, at the stage of a raw material or an intermediate. Thereafter, the protecting group may be removed, if necessary, to obtain a desired compound of the present invention or a pharmaceutically acceptable salt thereof, or its intermediate. Examples of such a functional group include an amino group, a carboxyl group, alkyne-CH (including an ethynyl group) and a hydroxy group. Examples of the protecting groups for these include those described in JOHN WILEY & SONS, "GREENE'S PROTECTIVE GROUPS IN ORGANIC SYNTHESIS (FOURTH EDITION)" written by T. Greene et al. These may be appropriately used depending upon the reaction conditions.

As to general guidance about reaction conditions and reagents, see, for example, JOHN WILEY & SONS, "MARCH'S ADVANCED ORGANIC CHEMISTRY (SIXTH EDITION)" written by J. MARCH et al. Typical methods for producing a compound of the present invention will be described below.

Hereinafter, unless otherwise specified, q, $R^1$, $R^2$, $R^3$, $R^4$, $R^5$, $R^6$, $R^7$, G, J, W, X, Y, Z and ring E are the same as mentioned above with respect to each of compounds of the present invention represented by the general formula (1) to the general formula (7) or pharmaceutically acceptable salts thereof. Requisite raw materials or intermediates can be obtained by a standard method of organic chemistry. Production of these raw materials or intermediates will be described in the examples described later, but not limited to those examples. Other requisite raw materials or intermediates can be obtained in the same manner as described in the examples. These can be easily produced by those skilled in the art of organic chemistry by applying various known synthesis methods.

Hereinafter, as a leaving group represented by L, a halogen atom such as a chlorine atom, a bromine atom, an iodine atom and a fluorine atom; an alkylsulfonyloxy group which may have one or more substituents such as a methanesulfonyloxy group, an ethanesulfonyloxy group, a propanesulfonyloxy group and a trifluoromethanesulfonyloxy group or an arylsulfonyloxy group which may have one or more substituents such as a p-toluenesulfonyloxy group, a benzenesulfonyloxy group and a p-bromobenzenesulfonyloxy group is mentioned. The same shall apply hereinafter.

Compounds of the present invention represented by the general formula (1) to the general formula (7) or pharmaceutically acceptable salts thereof can be produced by a method known per se or a method in accordance with the known method, for example, a method represented by e.g., the following reaction scheme A or reaction scheme B.

Production Method A

Reaction scheme A

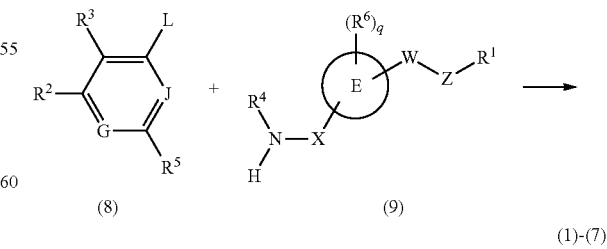

<Formula 8>

(8)　　(9)

(1)-(7)

[Step A]

This is a step of reacting a compound (8) with a compound (9) [hereinafter, including a salt of the compound (9)] to obtain a compound of the present invention represented by each of the general formula (1) to the general formula (7) or a pharmaceutically acceptable salt thereof. When the compound (8) and the compound (9) are commercially available, commercially available products may be directly used or the compounds may be produced by e.g., a method known per se or a method in accordance with the known method.

(Group)

As the leaving group L used in this reaction, a chlorine atom is preferable. As $R^4$ of this reaction, a hydrogen atom is preferable.

(Solvent)

This reaction is advantageously performed in the absence of a solvent or in the presence of a solvent that has no influence on the reaction. These solvents are not particularly limited as long as the reaction proceeds, and include an aromatic hydrocarbon such as benzene, toluene, xylene or chlorobenzene, an ether such as diethyl ether, tetrahydrofuran (THF), 1,2-dimethoxyethane (DME), dioxane or diisopropyl ether, a halogenated hydrocarbon such as dichloromethane, 1,2-dichloroethane, chloroform, carbon tetrachloride or tetrachloroethane, a ketone such as acetone or methyl ethyl ketone, a sulfoxide such as dimethylsulfoxide (DMSO), an amide such as N,N-dimethylformamide (DMF), N,N-dimethylacetamide (DMA), N-methyl-2-pyrrolidone (NMP) or formamide, an alcohol such as methanol, ethanol, isopropyl alcohol, propyl alcohol, tert-butanol, benzyl alcohol or amyl alcohol, an alkane such as hexane, cyclohexane or pentane, acetonitrile, ethyl acetate, dimethylimidazolidinone (DMI), ethylene glycol, diethylene glycol dimethyl ether, hexamethylphosphoric triamide, hexamethylphosphoramide (HMPA), quinoline, water, or a mixture of two or more of these. This reaction may be performed preferably in the presence of toluene, N-methyl-2-pyrrolidone (NMP) or N,N-dimethylformamide (DMF).

(Base)

Depending upon the compound, it is sometimes advantageous that the reaction is performed in the presence of a base, for example, an organic base such as diethylamine, triethylamine, N,N-diisopropylethylamine, diisopropylamine, pyridine, 4-(N,N-dimethylamino)pyridine, aniline, N,N-dimethylaniline, N,N-diethylaniline, piperidine, N-ethylpiperidine, N-methylmorpholine, morpholine, pyrrolidine, trimethylamine, butylamine, tributylamine, ammonia, picoline, 2,6-lutidine, 1,8-diazabicyclo[5.4.0]undec-7-ene, a metal salt base (e.g., potassium carbonate, sodium hydroxide, sodium hydrogencarbonate, a basic alumina, potassium hydrogencarbonate, potassium hydroxide, sodium carbonate, sodium methoxide, sodium ethoxide, potassium tert-butoxide, butyllithium, calcium carbonate, cesium carbonate), or a metal hydride (e.g., sodium hydride, potassium hydride). This reaction may preferably be performed in the presence of triethylamine.

(Reaction Conditions)

In this reaction, the compound (8) and the compound (9) are used in equivalent moles or one of them is used in an excessive amount. The reaction can be performed at any temperatures, whether cooled or heated under reflux, which can appropriately be set depending upon the compound. The reaction temperature is usually about −80° C. to 145° C. and preferably about 10° C. to 115° C.

Production Method B

Reaction scheme B

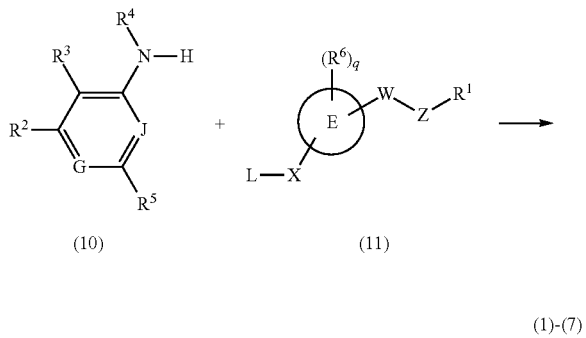

<Formula 9>

(10)      (11)

(1)-(7)

[Step B]

This is a step of reacting a compound (10) with a compound (II) to obtain a compound of the present invention represented by each of the general formula (1) to the general formula (7) or a pharmaceutically acceptable salt thereof. When the compound (10) and the compound (II) are commercially available, commercially available products may be directly used or the compounds may be produced by e.g., a method known per se or a method in accordance with the known method.

(Group)

As the leaving group L used in this reaction, a bromine atom or a chlorine atom is preferable. As $R^4$ of this reaction, a hydrogen atom is preferable.

(Solvent)

This reaction is advantageously performed in the absence of a solvent or in the presence of a solvent that has no influence on the reaction. These solvents in this reaction are not particularly limited as long as the reaction proceeds. The reaction is performed in each of a solvent as mentioned above and preferably performed in the presence of tetrahydrofuran (THF), toluene, N,N-dimethylformamide (DMF), dimethylsulfoxide (DMSO), acetonitrile, chloroform, dichloromethane, or N-methyl-2-pyrrolidone (NMP).

(Base)

Depending upon a compound, it is sometimes advantageous if the reaction is carried out in the presence of the base. The reaction may be performed in the presence of a base, preferably potassium carbonate, sodium hydrogencarbonate, triethylamine, N,N-diisopropylethylamine, basic alumina, sodium carbonate, cesium carbonate, sodium hydroxide or sodium hydride.

(Reaction Conditions)

In this reaction, the compound (10) and the compound (11) are used in equivalent moles or one of them is used in an excessive amount. The reaction can be performed at any temperatures whether cooled or heated under reflux and the reaction condition can be appropriately set depending upon the compound. The reaction temperature is usually about −80° C. to 153° C. and preferably about −20° C. to 115° C.

Prestep 1

Reaction scheme C

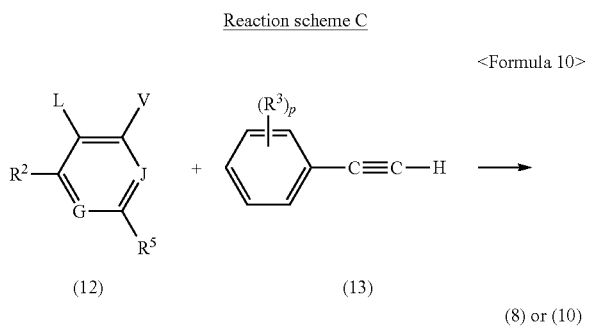

<Formula 10>

(12)       (13)

(8) or (10)

wherein L is a leaving group (preferably an iodine atom or a bromine atom), V is an amino group which may have one or more substituents (e.g., an amino group, a methylamino group, an ethylamino group, an isopropylamino group, a tert-butoxycarbonylamino group, an ethoxycarbonylamino group, an acetylamino group, a methanesulfonamide group, a benzenesulfonamide group) or a leaving group (preferably a chlorine atom), p is any one of integers of 0, 1, 2, and 3, when p is 2 or more, the groups represented by $R^3$ are the same or different.

[Prestep 1]

This is a step of reacting a compound (12) and a compound (13) to obtain the compound (8) or (10). This step for producing a compound (8) or (10) may be performed, if necessarily, before [Step A] or [Step B] (preferably before [Step B]). In this reaction, the compound (12) and the compound (13) are usually reacted in the presence of at least one appropriate metal catalyst and a base. When the compound (12) and the compound (13) are commercially available, commercially available products may be directly used or they may be produced by e.g., a method known per se or a method in accordance with the known method.

(Metal Catalyst)

As the metal catalyst, a palladium catalyst and/or a copper catalyst can be used and preferably a palladium catalyst and a copper catalyst are used in combination. Examples of the palladium catalyst used in this reaction include dichlorobis(triphenylphosphine)palladium, dichloro bis(benzonitrile) palladium, palladium acetate, tetrakis(triphenylphosphine) palladium, tris(dibenzylideneacetone)dipalladium, palladium carbon, palladium chloride and the like. Preferably, palladium chloride, palladium acetate, dichlorobis(triphenylphosphine)palladium, and tetrakis(triphenylphosphine)palladium may be used. Examples of the copper catalyst used in this reaction include cuprous iodide, cuprous chloride, cuprous oxide and cuprous bromide. Preferably, cuprous iodide may be used.

(Solvent)

It is advantageous that this reaction is performed in the absence of a solvent or in the presence of an appropriate solvent that has no influence on the reaction. In this reaction, the solvents are not particularly limited as long as the reaction proceeds. The reaction may be performed in a solvent as mentioned above, preferably in the presence of toluene, tetrahydrofuran (THF), 1,2-dimethoxyethane (DME), N,N-dimethylformamide (DMF), N-methyl-2-pyrrolidone (NMP) and/or acetonitrile, and further preferably, in the presence of toluene, tetrahydrofuran (THF), 1,2-dimethoxyethane (DME) or N,N-dimethylformamide (DMF).

(Base)

The base used in this reaction is not particularly limited as long as the reaction proceeds. The reaction may be performed in a base as mentioned above, preferably performed in the presence of diethylamine, triethylamine, diisopropylamine, N,N-diisopropylethylamine, pyridine, pyrrolidine or piperidine, and further preferably performed in the presence of pyridine, triethylamine, diisopropylamine or pyrrolidine. Furthermore, a base may serve as a solvent.

(Reaction Conditions)

In this reaction, the compound (12) and the compound (13) are used in equivalent moles or one of them is used in an excessive amount. The reaction can be performed at any temperatures, whether cooled or heated under reflux, which can appropriately be set depending upon the compound. The reaction temperature is usually about −100° C. to 160° C., preferably about 10° C. to 140° C.

(Purification)

A product can be used in the next reaction in the state of a reaction solution or as a crude product, or isolated from the reaction mixture in accordance with a conventional method.

(Removal of Protecting Group)

Furthermore, if V in the formula is an amino group which may have one or more substituents having a protecting group such as a tert-butoxycarbonylamino group, an ethoxycarbonylamino group, an acetylamino group, a methanesulfonamide group or a benzenesulfonamide group, the protecting group may be removed after completion of the reaction of [Prestep 1]. The protecting group may be removed by e.g., a method known per se or a method in accordance with the known method (for example, acid treatment with trifluoroacetic acid, hydrolysis with sodium hydroxide, or reduction).

(Modification of Prestep 1)

Furthermore, in [Prestep 1], a corresponding alkynyl metal compound (for example, a copper acetylide compound, a sodium tetraethynylaluminate compound (also referred to as sodium tetraalkynylaluminate compound), ethynylzinc bromide, ethynylzinc chloride, ethynylzinc iodide, ethynylmagnesium bromide, ethynylmagnesium chloride and like others), in place of a copper catalyst and the compound (13), can be reacted with the compound (12) in a solvent and/or a base to obtain the compound (8) or (10).

(Alternative for Prestep 1)

Furthermore, the compound (8) or (10) may be obtained by the Stille reaction in place of [Prestep 1]. The Stille reaction can be performed by a conventional method in the presence of a palladium catalyst. As the palladium catalyst used in the Stille reaction, dichlorobis(triphenylphosphine) palladium, tetrakis(triphenylphosphine)palladium or tris (dibenzylideneacetone)dipalladium is preferable. The reaction is performed at any temperatures, whether cooled or heated under reflux, which can be appropriately set depending upon a compound.

(Synthesis of Other Compounds)

Furthermore, depending upon the compound, in place of [Prestep 1] (including the Sonogashira reaction) and modification of Prestep 1 (including the Negishi reaction), synthesis may be performed in accordance with a reaction such as the Heck reaction, the Suzuki coupling reaction, the Ullmann reaction, the Wittig reaction, the Horner-Emmons reaction or the Knoevenagel reaction, or methods according to these. These reactions can be performed by a conventional method. For example, in the Wittig reaction, in place of leaving group L of the compound (12), an acyl group such as a formyl group, an acetyl group, a propionyl group or a butyryl group is preferable and in place of the compound (13), the corresponding phosphorus ylide is used.

Prestep 2

Reaction scheme D

<Formula 11>

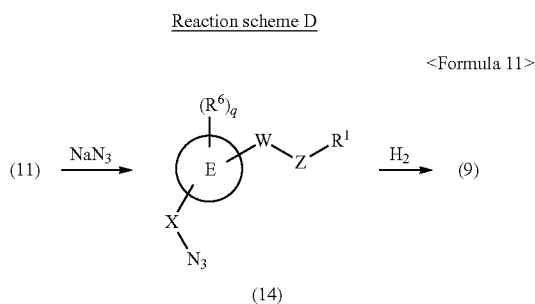

[Prestep 2]

When the compound (9) is commercially available, a commercially available product may be directly used. Furthermore, the compound (9) may be produced by e.g., a method known per se or a method in accordance with the known method. The compound (9) can be produced by a conventional method. For example, the compound (9) may be produced, as shown in Reaction scheme D, by a method in which the corresponding organic halide compound (for example, a compound (11)) and $NaN_3$ are reacted in a solvent as mentioned above (for example, DMF), (the reaction is performed at any temperature, whether cooled or heated under reflux, which is appropriately set depending upon the compound) to obtain an azide compound (e.g., a compound (14)), which is then reduced (for example, reduction by a metal catalyst such as Lindlar catalyst, Rosenmund catalyst or Raney nickel and hydrogen, and reduction by sodium borohydride) or a method in accordance with this. A reductive reaction by a metal catalyst may be performed in a solvent as mentioned above. The reductive reaction by Lindlar catalyst ($Pd-CaCO_3-PbO$) may be performed by catalytic hydrogenation in a solvent as mentioned above (for example, ethanol, methanol, isopropyl alcohol, hexane, diethyl ether, THF). The reductive reaction by Rosenmund catalyst ($Pd-BaSO_4$) is performed by catalytic hydrogenation in a solvent as mentioned above (for example, xylene, toluene). The reductive reaction by a metal catalyst such as Raney nickel is performed by catalytic hydrogenation in the solvent as mentioned above (for example, ethanol, methanol, isopropyl alcohol). The catalytic hydrogenation mentioned above may be performed under hydrogen atmosphere conditions or under pressurized hydrogen conditions using a pressurized vessel (e.g., an autoclave, a pressure resistant glass container). Furthermore, the catalytic hydrogenation (particularly, Raney nickel is used as a metal catalyst) mentioned above sometimes advantageously proceeds if the catalytic hydrogenation is performed in a solvent as mentioned above in the presence of the base (for example, ammonia water). The reductive reaction by sodium borohydride may be performed in a solvent as mentioned above (for example, ethanol, methanol, isopropyl alcohol, THF, diethyl ether) preferably in ethanol. Furthermore, depending upon the compound, production can be made in accordance with the Gabriel synthesis, a reductive alkylation reaction (e.g., the Leuckart reaction, the Wallach reaction) of ammonia or an amine, or a method of treating the corresponding imine or nitrile with a reducing agent (e.g., a metal catalyst such as palladium carbon or Raney nickel or other catalysts as mentioned above).

Furthermore, a reductive reaction may be performed in the process for producing a compound of the present invention, a compound (9) or a compound (II). Such a reductive reaction may be performed by a method known per se.

Furthermore, e.g., hydrolysis, esterification or transesterification may be performed in the process for producing a compound of the present invention, a compound (9) or a compound (II). Such hydrolysis, esterification or transesterification may be performed in accordance with a method known per se.

Furthermore, amidation may be performed in the process for producing a compound of the present invention, a compound (9) or a compound (II). Such amidation may be performed in accordance with a method known per se.

Most of intermediates defined in the specification, for example, a compound (8), a compound (9), a compound (10), a compound (12), and a compound (14) are novel compounds and provided as another aspect of the present invention.

A compound of the present invention thus produced can be purified and/or isolated by a known method, for example, extraction, chromatography, recrystallization, filtration, reduced-pressure distillation, precipitation and dehydration.

Furthermore, a compound of the present invention is obtained by a production method as mentioned above in the form of free base or a salt with an acid. To obtain a free base from the salt, a salt of a compound of the present invention may be treated with an appropriate base mentioned above in accordance with a conventional method. Furthermore, to obtain a salt of a compound of the present invention, e.g., an acid addition salt, the obtained salt of a compound of the present invention may be treated with an appropriate acid as mentioned above in accordance with a conventional method.

{General Evaluation Test Method}

A compound of the present invention or a pharmaceutically acceptable salt thereof has anti-cell-proliferation activity, for example, anticancer activity, which is conceivably also derived from the receptor tyrosine kinase inhibitory activity of the compound. These properties may be evaluated by one or more methods, for example, shown below.

(a) In vitro assay for measuring the effect of a test compound in inhibiting the enzyme EGF receptor tyrosine kinase Receptor tyrosine kinase was obtained from A-431 cells (derived from human vulval carcinoma) in partially purified form by a method relevant to a method shown in Carpenter et al., J. Biol. Chem., 1979, 254, 4884, Cohen et. al., J. Biol. Chem., 1982, 257, 1523, and Braun et al., J. Biol. Chem., 1984, 259, 2051.

A-431 cells were grown in Dulbecco's modified Eagle's medium (DMEM) containing 5% fetal calf serum (FCS) up to a confluent state. The resultant cells were homogenized in a hypotonic borate/EDTA buffer (pH 10.1). The homogenate was centrifuged at 400×g for 10 minutes at 0° C. to 4° C. The supernatant was centrifuged at 25,000×g for 30 minutes at 0° C. to 4° C. The resultant pelleted material was suspended in 30 mM HEPES buffer (pH 7.4) containing 5% glycerol, 4 mM benzamidine and 1% Triton X-100, stirred at 0° C. to 4° C. for one hour, and centrifuged again at 100,000×g for one hour at 0° C. to 4° C. The supernatant containing solubilized receptor tyrosine kinase was stored in liquid nitrogen.

For test purposes, the enzyme solution (40 μl) thus obtained was added to the following mixture: a mixture of a mixture (400 μl) of 150 mM HEPES buffer (pH 7.4), 500 μM sodium orthovanadate, 0.1% Triton X-100, 10% glycerol, water (200 μl), 25 mM DTT (80 μl) and a mixture (80 μl) of 12.5 mM manganese chloride, 125 mM magnesium chloride and distilled water. In this manner, a test enzyme solution was obtained.

Each test compound was dissolved in dimethylsulfoxide (DMSO) to obtain a 50 mM solution which was diluted with 40 mM HEPES buffer containing 0.1% Triton X-100, 10% glycerol and 10% DMSO to obtain a 500 µM solution. This solution was mixed with a solution of epidermal growth factor (EGF; 20 µg/ml) in the same volume. In this manner, a test compound/EGF mixture solution was obtained.

[γ-$^{32}$P]ATP (3000 Ci/mM, 250 µCi) was diluted by addition of an ATP solution (100 µM) in distilled water to obtain a solution of 2 ml in volume. A 4 mg/ml solution of a peptide (Arg-Arg-Leu-Ile-Glu-Asp-Ala-Glu-Tyr-Ala-Ala-Arg-Gly) in a mixture of 40 mM HEPES buffer (pH 7.4), 0.1% Triton X-100 and 10% glycerol was added in the same volume. In this manner, an ATP/peptide mixture was obtained.

The test compound/EGF mixture solution (5 µl) was added to the test enzyme solution (10 µl) and the mixture was incubated at 0° C. to 4° C. for 30 minutes. The ATP/peptide mixture (10 µl) was added and the resultant mixture was incubated at 25° C. for 10 minutes. 5% trichloroacetic acid (40 µl) and bovine serum albumin (BSA; 1 mg/ml, 5 µl) were added to terminate a phosphorylation reaction. The mixture was allowed to stand still at 4° C. for 30 minutes and then centrifuged. An aliquot (40 µl) was taken from the supernatant and placed on a Whatman p81 phosphocellulose paper-filter piece. The paper-filter piece was washed in 75 mM phosphoric acid (10 ml) and repeated 4 times and dried. Radioactivity present in the paper-filter was measured by a liquid scintillation counter (Sequence A). The reaction sequence was repeated in the absence of EGF (sequence B) and repeated again in the absence of a test compound (sequence C). Receptor tyrosine kinase inhibition was indicated by inhibition ratio (%), which was calculated in accordance with the following equation, provided that the measurement results of sequence A is expressed by SA, the measurement results of sequence B by SB, and the measurement results of sequence C by SC. Inhibition ratio (%)=100×{(SC−SB)−(SA−SB)}/(SC−SB). Subsequently, within a concentration range of a test compound providing IC$_{50}$ value, the extent of inhibition was determined.

(b) In vitro assay for measuring the effect of a test compound in inhibiting growth of human nasopharyngeal cancer cell line KB by EGF-stimulation KB cells were seeded into wells at a density of 1×10$^4$ to 1.5×10$^4$ cells per well and grown in DMEM supplemented with 5% FCS (charcoal-stripped) for 24 hours. After incubation for 3 days, cell growth was determined based on the extent of blue color occurrence, which was produced by metabolizing a MTT tetrazolium dye. Subsequently, cell growth was determined in the presence of EGF (10 ng/ml) or in the presence of EGF (10 ng/ml) and a test compound within a predetermined concentration range. Then, an IC$_{50}$ value could be calculated.

(c) In vivo assay for measuring the effect of a test compound (usually, ball-milled, prepared as a suspension in 0.5% polysorbate, and orally administered) in inhibiting liver cell growth stimulation induced by administration of growth factor TGFα (subcutaneous administration of 400 µg/kg, i.e., twice a usual dose, 3 hours and 7 hours respectively after administration of the test compound) in a group of male rats In a control group of rats, administration of TGFα causes liver cell growth stimulation as large as on average 5 times.

Cell growth of control animals and test animals was measured in accordance with the following manner:

On the morning of the day after a test compound (or 0.5% polysorbate in a control group) was administered, bromodeoxyuridine (BrdU; intraperitoneally 100 mg/kg) was administered to animals. Four hours later, the animals were killed and the livers were excised out. Slices were cut out from each liver, and BrdU uptake was measured in the same manner as in conventional immunohistological techniques described below:

Goldsworthy et al., Chemically Induced Cell Proliferation: Implications for Risk Assessment, Wiley-Liss Inc., 1991, pp. 253-284 (267 and 268 in a Japanese translation). To calculate an approximate ED$_{50}$ value on inhibition of liver cell proliferation measured by inhibition of BrdU uptake, tests were further performed using the test compound within a predetermined dose range.

(d) In vivo assay on a group of athymic nude mice (strain ONU: Alpk) for determining the effect of a test compound (usually, ball-milled, prepared as a suspension in 0.5% polysorbate, and orally administered) in inhibiting the growth of xenografts of the human vulval epidermoid carcinoma cell line A-431

A-431 cells were maintained in a cultured product in DMEM having 5% FCS and 2 mM glutamine supplemented thereto. Freshly cultured cells were harvested by trypsinization and subcutaneously injected into both flanks of each of many donor nude mice (10000000 cells/0.1 ml/mouse). When a sufficient amount of tumorigen was obtained (about 9 to 14 days later), fragments of tumor tissue were transplanted in the flanks of recipient nude mice (test day 0). Usually, on the 7th day after the transplantation (test day 7), groups of 7 to 10 mice having comparable sizes of tumor were selected. To these groups of mice, administration of the test compound was commenced. The test compound was administered once per day continuously for 13 days in total (including test day 7 to 19). In some tests, administration of the test compound was continued beyond test day 19, for example, to test day 26. In each case, the animals were killed on the following day and final tumor volume was calculated from the measurement values of the length and width of the tumors. The suppression percentage was calculated from the resultant tumor volume based on the control (untreated).

The pharmacological properties of a compound of the present invention vary depending upon structural change as expected. Generally, the activity that a compound of the present invention can be demonstrated by at least one of the following concentrations or doses of the above tests (a), (b), (c) and (d):

Test (a): IC$_{50}$ in the range of, for example, 0.01 µM to 1 µM;

Test (b): IC$_{50}$ in the range of, for example, 0.1 µM to 10 µM;

Test (c): ED$_{50}$ in the range of, for example, 1 mg/kg to 100 mg/kg;

Test (d): Tumor volume suppression 20% to 70% at a daily dose in the range of, for example, 50 mg/kg to 400 mg/kg.

Therefore, for example, in the case where a compound is ethyl 5-(6-methyl-5-{[4-(trifluoromethyl)phenyl]ethynyl}pyrimidin-4-ylaminomethyl)-2-furancarboxylate, IC$_{50}$ is 0.24 µM in Test (a), IC$_{50}$ is 0.8 µM in Test (b), ED$_{50}$ is less than 12.1 mg/kg in Test (c), and a suppression rate is 68% at a dose of 50 mg/day/weight (kg) in Test (d).

Furthermore, for example, in the case where a compound is methyl 5-(6-methyl-5-{[4-(trifluoromethyl)phenyl]ethynyl}pyrimidin-4-ylaminomethyl)-2-furancarboxylate, IC$_{50}$ is 0.22 µM in Test (a), IC$_{50}$ is 0.7 µM in Test (b), ED$_{50}$ is less than 11.8 mg/kg in Test (c), and a suppression rate is 69% at a dose of 50 mg/day/weight (kg) in Test (d).

Therefore, a compound of the present invention or a pharmaceutically acceptable salt thereof has anti-cell-proliferation activity (particularly, anti-cell-proliferation activity selective to malignant cells such as cancer cells) and the properties are conceivably derived from a tyrosine kinase inhibitory activity thereof. Therefore, a compound of the present invention or a pharmaceutically acceptable salt thereof can be used for obtaining a tyrosine kinase inhibitory effect in warm-blooded animals (for example, humans, horses, cows, dogs, cats, rats, mice, rabbits, pigs, monkeys, etc.). More specifically, a compound of the present invention or a pharmaceutically acceptable salt thereof is expected to usefully work in treating a disease or a medical condition in which tyrosine kinases are involved.

{General Use}

A compound of the present invention or a pharmaceutically acceptable salt thereof provides a method for treating malignant cell proliferation. A compound of the present invention or a pharmaceutically acceptable salt thereof is characterized by inhibiting a tyrosine kinase activity. Since tyrosine kinases are generally involved in many types of cancers of warm-blooded animals, for example, human cancers such as leukemia (e.g., chronic myelocytic leukemia (CML), acute lymphocytic leukemia, Philadelphia chromosome positive acute lymphocytic leukemia, chronic myelomonocytic leukemia (CMML), acute myelocytic leukemia), brain tumor as well as cancers of the lung, pancreas, colon, rectum, duodenum, esophagus, tongue, pharynx, stomach, breast, prostate, bladder, uterus and ovary, a compound of the present invention or a pharmaceutically acceptable salt thereof is expected to have anticancer properties in a wide range. Furthermore, a compound of the present invention or a pharmaceutically acceptable salt thereof provides an anti-cell-proliferation effect and thereby expected to have an activity against a wide range of leukemia, a malignant lymphoid disease as well as tumors (for example, carcinoma and sarcoma of tissues such as the breast, lung, colon, rectum, stomach, prostate, bladder, pancreas and ovary).

Furthermore, a compound of the present invention or a pharmaceutically acceptable salt thereof is expected to have efficacy to other cell proliferative diseases such as psoriasis and rheumatism. Furthermore, examples of a disease in which an abnormal tyrosine kinase activity is involved include cardiovascular diseases, diabetic complications, osteoporosis and Alzheimer's disease. Therefore, a compound of the present invention or a pharmaceutically acceptable salt thereof can be used as a prophylactic agent and/or therapeutic agent for cardiovascular diseases such as restenosis and diabetic complications such as diabetic retinopathy. Furthermore, a compound of the present invention or a pharmaceutically acceptable salt thereof can be used as a therapeutic agent and/or prophylactic agent for diseases mainly caused by an allergic response or inflammation response, for example, rhinitis such as pollinosis and allergic rhinitis, asthma such as the allergic asthma and bronchial asthma, pneumonia, tympanitis, atopic dermatitis, contact dermatitis, urticaria, food allergy, conjunctivitis, vernal catarrh, fibrotic disease, osteoarthritis, ulcer, systemic lupus erythematosus and rejection response at the time of organ transplantation.

Therefore, according this aspect of the present invention, there is provided use of the compound of the present invention or a pharmaceutically acceptable salt thereof mentioned above in the manufacture of a medicament for use in the production of an anti-cell-proliferation effect in a warm-blooded animal (for example, a human).

According another aspect of the present invention, there is provided a method for producing an anti-cell-proliferation effect in a warm-blooded animal (including, for example, a warm-blooded animal having cancer cells, a warm-blooded animal having stem cells transplanted) in need of such a treatment, for example, in a human, including administering an effective amount of the compound of the present invention or a pharmaceutically acceptable salt thereof mentioned above to a warm-blooded animal.

Furthermore, according to another aspect of the present invention, there is provided use for the manufacture of a medicament for use in the production during culture (which may include cell differentiation) of warm-blooded animal (for example, human) cells [including: stem cells (for example, iPS cells (which are also referred to as artificial pluripotent stem cells, embryonic stem cell-like cells, ES cell-like cells, or induced pluripotent stem cells, which are derived from somatic cells, and which are characterized by being obtainable without using germ cells and embryonic stem (ES) cells and having pluripotency, i.e., ability to differentiate into plural types of cells present in a living body, and proliferation ability) and ES cells (e.g., embryonic stem cells) and hematopoietic stem cells, mesenchymal stem cells, neural stem cells, basal cells and liver stem cells) and other somatic cells; all cells present in a living body, which may be differentiated and induced cells; and artificially manipulated cells such as somatic cells having one or more arbitrary genes and/or one or more arbitrary chemical substances introduced therein] of an anticancer effect (i.e., a tyrosine kinase inhibitory effect, an effect of preventing cells from converting into cancer cells and/or an anti-cell-proliferation effect, particularly an effect of selectively suppressing proliferation of cancer cells but rarely suppressing proliferation of normal cells) in these cells, or in the production of an anti-cell-proliferation effect during the cell culture process.

Furthermore, according to another aspect of the present invention, there is provided a method for obtaining an anticancer effect during a process for culturing warm-blooded animal cells, for example, a process for culturing human cells, including adding an effective amount of the compound of the present invention or a pharmaceutically acceptable salt thereof mentioned above to a medium (including e.g., a culture solution, buffer) for culturing warm-blooded animal cells.

(Combination Use with Other Pharmaceutical Products)

The anti-cell-proliferation treatment mentioned above may be applied as a monotherapy. Otherwise, a compound of the present invention or a pharmaceutically acceptable salt thereof may be used in combination with one or two or more other medicaments and/or Chinese medicines, for example, those selected from the following examples including monoclonal antibodies such as trastuzumab (Herceptin (trademark)), rituximab (Rituxan (trademark)), bevacizumab (Avastin (trademark)) and cetuximab (Erbitux (trademark)); molecular-targeted drugs (e.g., tyrosine kinase inhibitor) such as gefitinib (Iressa (trademark)), imatinib, imatinib mesylate (Glivec (trademark)), erlotinib and erlotinib hydrochloride (Tarceva (trademark)); differentiation-inducing agents such as hexamethylene bisacetamide and all-trans retinoic acid (ATRA), i.e., tretinoin and retinoic acid (vitamin A acid); cytokines such as interferons (IFNα, IFNβ, IFNγ) and interleukin (IL-2); plant-derived anticancer agents such as etoposide, paclitaxel (Taxol (trademark)), docetaxel (Taxotere (trademark)), camptothecin, topotecan, irinotecan, vinblastine, vincristine sulfate (Oncovin (trademark)), vinorelbine and vindesine; alkylating agents such as nitrogen mustard, hydrochloric acid nitrogen-mustard-N-oxide (nitrogen mustard-N-oxide hydrochloride), cyclophosphamide (Endoxan (trademark)), ifosfamide, nimustine, nimustine hydrochloride, ranimustine, thiotepa, dacarbazine, lomustine, prednimustine and melphalan; platinum drugs such as nedaplatin, cisplatin, carboplatin and oxaliplatin; antimetabolites such as enocitabine, methotrexate, 5-fluorouracil, tegafur (Futraful (trademark)), UFT, doxifluridine, carmofur, galocitabine, emitefur, cytarabine, cytarabine ocfosfate hydrate, 6-mercaptopurine, thioinosine, azathioprine, hydroxycarbamide, fludarabine, fludarabine phosphate (Fludara (trademark)), gemcitabine hydrochloride, pentostatin, 6-mercaptopurine riboside, Alkeran (trademark), gemcitabine, pemetrexed and pemetrexed sodium hydrate; hormonal anticancer agents such as LH-RH agonists (e.g., buserelin, buserelin acetate, goserelin, goserelin acetate, leuprorelin, leuprorelin acetate), aromatase inhibitors (e.g., anastrozole, exemestane), luteal hormone (e.g., medroxyprogesterone), antiestrogens (e.g., tamoxifen) and antiandrogens (e.g., flutamide, bicalutamide, nilutamide); anticancer antibiotics such as aclarubicin, actinomycin C, actinomycin D (Cosmegen (trademark)), mitomycin C, mitoxantrone, mitoxantrone hydrochloride, bleomycin, bleomycin hydrochloride, bleomycin sulfate, adriamycin, toyomycin (chromomycin), and anthracycline based anticancer agents (e.g., daunorubicin, daunorubicin hydrochloride, doxorubicin, doxorubicin hydrochloride, pirarubicin, pirarubicin hydrochloride, epirubicin, epirubicin hydrochloride, amrubicin, amrubicin hydrochloride); anticancer steroids such as testosterone, testosterone enanthate, chlormadinone, chlormadinone acetate and mepitiostane; antiemetics such as dexamethasone, granisetron and ondansetron. Besides the medicaments mentioned above, combination use with topoisomerase inhibitors (e.g., irinotecan hydrochloride), hormones (e.g., prednisolone, prednisone), poisoning therapeutic agents (e.g., calcium levofolinate), antibacterial agents (e.g., Leucovorin (trademark), bleomycin); or other anticancer agents (e.g., thalidomide, procarbazine, sorafenib, sorafenib tosylate (Nexavar (trademark)), sunitinib, sunitinib malate (Sutent (trademark)) may be made.

{General Preparation (Manufacture of Medicament) Method}

Such a combination therapy can be attained by simultaneous, sequential or separate administration of individual therapeutic components. According to this aspect of the present invention, there is provided a preparation containing a compound of the present invention or a pharmaceutically acceptable salt thereof and an additional medicament as mentioned above for combination therapy for cancer.

In addition to a compound of the present invention or a pharmaceutically acceptable salt thereof and a composition of a medicament containing a compound of the present invention or a pharmaceutically acceptable salt thereof, another pharmacologically active compounds can be contained. Furthermore, these pharmaceutical compositions may contain a plurality of compounds of the present invention or pharmaceutically acceptable salts thereof. Furthermore, a pharmaceutical composition containing a compound of the present invention or a pharmaceutically acceptable salt thereof and a pharmaceutical composition containing a prodrug of a compound of the present invention or a pharmaceutically acceptable salt thereof can be produced according to a method known per se.

When a medicament containing a compound of the present invention or a pharmaceutically acceptable salt thereof is administered to a warm-blooded animal such as a human, one can use a variety of administration modes, including both parenteral administration modes (e.g., intravenous, subcutaneous, intramuscular, intravascular, intraorgan, intranasal, intradermal, extraocular, intraocular, cerebral, rectal, intraperitoneal (including intravaginal) and intratumoral administration forms as well as administration to tumor proximal site or direct intralesional administration) adopting the form of injection (including e.g., drip infusion), ointment, suppository, ophthalmic suspension, eye ointment, transdermal liquid medicine, transdermal patch, transmucosal liquid medicine, transmucosal patch, inhalation, pellet, etc.; and oral administration modes adopting the form of tablet (including sugar-coated tablet, film coated tablet), capsule (including soft capsule, micro capsule), granule, pill, syrup, elixir, fine granule, powder, etc. While the administration form of a compound of the present invention may be either oral or parenteral as mentioned above, oral administration in the form of tablet or capsule, or parenteral administration in the form of injection is preferable.

A clinical dose of a compound of the present invention or a pharmaceutically acceptable salt thereof varies depending upon e.g., dosage form, administration time, administration interval, the age, sex, body weight and sensitivity of a patient, and the degree of symptom; however, usually, in the case of oral administration, an effective daily dose is about 0.001 mg/kg to 250 mg/kg body weight, preferably about 0.1 mg/kg to 100 mg/kg, further preferably about 1 mg/kg to 50 mg/kg. This is administered at a time or separately 2 to 4 times. In the case of intravenous administration, the daily dose is appropriately about 0.001 mg/kg to 30 mg/kg body weight, and administered at a time to separately a plurality of times per day. Furthermore, in the case of inhalant or transmucous agent, about 0.001 mg/kg to 25 mg/kg body weight is administered at a time to several times per day. However, if necessary, a dose outside the aforementioned range can be used. A compound of the present invention is produced into a preparation for administration by a conventional pharmaceutical means.

Solid preparations for oral administration (e.g., tablets, capsules, granules, pills, fine granules, powders) are produced by using one or more active substances (including a compound of the present invention or a pharmaceutically acceptable salt thereof) and one or more inactive substances in accordance with a method known per se. Examples of the inactive substances include excipients (for example, lactose, glucose, starch, mannitol, white sugar), binders (for example, mannitol, sorbitol, methylcellulose, polyvinylpyrrolidone, hydroxypropylmethylcellulose, hydroxypropylcellulose, gum arabic, gelatin, syrup), disintegrators (for example, starch, microcrystalline cellulose, carboxymethylcellulose, calcium carboxymethylcellulose, croscarmellose sodium, carmellose calcium, polyethylene glycol), and lubricants (for example, magnesium stearate, calcium stearate, talc, silica).

A tablet or a pill, if necessary, may be coated with a sugar coating (the material for coating film is not particularly limited as long as it contains sugar, and sugar such as sucrose, white sugar, erythritol, aspartame, trehalose, maltitol, mannitol, sorbit, xylitol and lactose may contain an inactive substance as mentioned above such as gelatin, gum arabic, talc, polyvinylpyrrolidone, polyethylene glycol, hydroxypropylcellulose, hydroxypropylmethylcellulose phthalate and/or titanium dioxide) or with a gastrosoluble or enteric film (for example, appropriate cellulose such as cellulose acetate phthalate or hydroxypropylmethylcellulose phthalate and an inert substance as mentioned may be contained). Furthermore, coloring matter (for example, titanium dioxide) may be used in coating for a tablet or a pill.

Liquid preparations (including, e.g., injection, solution, suspension, emulsion, aerosol, syrup, elixir) are prepared by a method known per se using one or more active substances (including a compound of the present invention or a pharmaceutically acceptable salt thereof) and a liquid medium. Examples of the liquid medium include water (including, e.g., distilled water for injection, physiological saline, purified water), alcohol (for example, ethanol, isopropyl alcohol, propylene glycol, polyethylene glycol), oil (for example, olive oil, corn oil, sesame oil, castor oil, peanut oil, cottonseed oil, liquid paraffin) and a derivative thereof.

Furthermore, a liquid preparation may contain additives such as a solubilizing agent (for example, triethanolamine, sodium carbonate, glutamic acid, aspartic acid, meglumine), a suspending agent, an emulsifier, a dispersing agent or a moistening agent (for example, gum arabic, tragacanth, sodium carboxymethylcellulose, methylcellulose, hydroxymethylcellulose, polyvinyl alcohol, polyvinylpyrrolidone, gelatin, lecithin, hyaluronic acid and a surfactant (for example, polyoxyethylene sorbitan fatty acid ester [Tween 80, Tween 60, by Atlas powder Co.], a polyoxyethylene castor oil derivative [HCO-60, HCO-50, by Nikko Chemicals Co., Ltd.], polysorbate 80, stearyl triethanolamine, sodium lauryl sulfate, lauryl-aminodipropionic acid, benzalkonium chloride, benzethonium chloride, glyceryl monostearate)), an isotonizing agent (for example, sodium chloride, glycerol, mannitol), a pH adjustor (for example, sodium hydroxide, hydrochloric acid), a buffer (for example, phosphoric acid and an alkali metal salt thereof, citric acid and an alkali metal salt thereof), a soothing agent (for example, benzyl alcohol), an antiseptic agent or a preservative (for example, methyl parahydroxybenzoate, ethyl parahydroxybenzoate, sorbic acid) and an antioxidant or a stabilizer (for example, ascorbic acid, sodium pyrosulfite). These additives are generally blended with a liquid preparation in a ratio usually used.

An injection can be obtained by dissolving, suspending or emulsifying a compound of the present invention or a pharmaceutically acceptable salt thereof and, if necessary, additives as mentioned above in a liquid medium. They may be dissolved, suspended or emulsified in any order and appropriately dissolved, suspended or emulsified in the same manner as in a method of producing a conventional injection. The content of a compound of the present invention or a pharmaceutically acceptable salt thereof in the injection is about 0.5 w/v % to 50 w/v %, preferably 1 w/v % to 20 w/v %.

An injection can be provided preferably as warmed and further subjected to, for example, sterilization by filtration, steam sterilization, irradiation sterilization and/or blending one or more sterilization agents in the same manner as in conventional injection. An injection is preferably autoclaved for sterilization, for example, at 2 times normal atmospheric pressure in water vapor (100° C. to 121° C.) conditions for 5 minutes to 30 minutes. Furthermore, an injection may be used by producing an aseptic injection material and dissolving, suspending or emulsifying it in an aseptic liquid medium before use.

An aerosol, a syrup, an elixir and the like may contain e.g., a sweetening agent (for example, aspartame, trehalose), a flavoring agent, a thickener and an aromatic.

REFERENCE EXAMPLES, EXAMPLES, PREPARATION EXAMPLES

The present invention will be more specifically described by way of Reference Examples, Examples and Preparation Examples; however, a compound of the present invention is not limited to the compounds described in the following Examples. Furthermore, a general method for producing raw materials and intermediates used in Examples will be described in Reference Examples.

Unless otherwise specified, the following conditions are used in Reference Examples, Examples and Preparation Examples.

(i) Operations were performed at room temperature. Furthermore, reactions may be performed in an inert gas atmosphere such as argon.

(ii) Evaporation was performed under vacuum by a rotary evaporator and work-up procedures were performed after residual solids, for example, a desiccant, were removed by filtration.

(iii) Washing may be performed with e.g., water, or a saturated aqueous solution of sodium hydrogencarbonate or sodium chloride.

(iv) Extraction may be performed with an extraction solvent such as dichloromethane, chloroform, ethyl acetate, diethyl ether or toluene.

(v) Examples of the packing material for column chromatography include silica gel, alumina, activated carbon and an ion exchange resin, and generally silica gel. Examples of the developing solvent (including an eluting solvent) for column chromatography include acetic acid, pyridine, water, methanol, ethanol, acetone, ethyl acetate, diethyl ether, chloroform, dichloromethane, benzene, carbon tetrachloride, toluene, hexane, cyclohexane and petroleum ether. Column chromatography may be performed by mixing these solvents (a plurality of solvents) in an arbitrary ratio (for example, a solvent mixture of chloroform and methanol).

(vi) Yields are sometimes described herein, which are shown for only explanation purpose and are not necessarily the maximum value that can be attained.

(vii) Mass spectra, which are measurement results by mass spectrometry (MS), are shown by a m/z value, which is a ratio of mass number (m) of a molecular ion relative to charge (z) of the molecular ion. Those mass spectra were measured by a method known per se such as electrospray ionization (ESI), atmospheric pressure chemical ionization (APCI) and fast atom bombardment (FAB).

(viii) In Preparation Examples, typical dosage forms containing a compound of the present invention or a pharmaceutically acceptable salt thereof and used for treating or preventing a disease in a human are shown, and formulations can be obtained by a conventional method known in the art of a medicament.

Reference Example 1

4-Amino-6-methyl-5-{[4-(trifluoromethyl)phenyl]ethynyl}pyrimidine

4-Amino-5-iodo-6-methylpyrimidine and cuprous 4-(trifluoromethyl)phenylacetylide were reacted in pyridine while stirring under heating to obtain a target substance. The target substance was subjected to e.g., proton nuclear magnetic resonance spectrometry ($^1$H-NMR) and mass spectrometry (MS) and confirmed as the titled compound. Furthermore, MS measurement result is shown.

Mass spectrum: 278.

Reference Example 2

4-Amino-6-methyl-5-{[4-(trifluoromethyl)phenyl]ethynyl}pyrimidine

5-Bromo-4-(tert-butoxycarbonylamino)-6-methylpyrimidine and sodium tetra{[4-(trifluoromethyl)phenyl]ethynyl}aluminate were reacted in tetrahydrofuran in the presence of dichlorobis(triphenylphosphine)palladium while stirring under heating to obtain a compound. To the compound, trifluoroacetic acid was added to remove a tert-butoxycarbonyl group serving as a protecting group to obtain a target substance. The target substance was subjected to e.g., proton nuclear magnetic resonance spectrometry ($^1$H-NMR) and mass spectrometry (MS) and confirmed as the titled compound. Furthermore, MS measurement result is shown.

Mass spectrum: 278.

Reference Example 3

4-Amino-6-methyl-5-{[4-(trifluoromethyl)phenyl]ethynyl}pyrimidine

The method described in Reference Example 2 was repeated except that 1,2-dimethoxyethane was used in place of tetrahydrofuran to obtain a target substance. The target substance was subjected to e.g., proton nuclear magnetic resonance spectrometry ($^1$H-NMR) and mass spectrometry (MS) and confirmed as the titled compound. Furthermore, MS measurement result is shown.

Mass spectrum: 278.

Reference Example 4

4-Amino-6-methyl-5-{[4-(trifluoromethyl)phenyl]ethynyl}pyrimidine 4-(tert-Butoxycarbonylamino)-5-iodo-6-methylpyrimidine and {4-(trifluoromethyl)phenyl]ethynylzinc bromide were reacted in a solvent mixture of tetrahydrofuran and N,N-dimethylformamide (1:1) in the presence of tetrakis(triphenylphosphine)palladium while stirring under room temperature to heating to obtain a compound. To the compound, trifluoroacetic acid was added to remove a tert-butoxycarbonyl group serving as a protecting group to obtain a target substance. The target substance was subjected to e.g., proton nuclear magnetic resonance spectrometry ($^1$H-NMR) and mass spectrometry (MS) and confirmed as the titled compound. Furthermore, MS measurement result is shown.

Mass spectrum: 278.

Reference Example 5

4-Chloro-6-methyl-5-{[4-(trifluoromethyl)phenyl]ethynyl}pyrimidine

4-Chloro-5-iodo-6-methylpyrimidine and [4-(trifluoromethyl)phenyl]ethynylzinc bromide were reacted in a solvent mixture of tetrahydrofuran and N,N-dimethylformamide (1:1) in the presence of tetrakis(triphenylphosphine)palladium while stirring under room temperature to heating to obtain a target substance. The target substance was subjected to e.g., proton nuclear magnetic resonance spectrometry ($^1$H-NMR) and mass spectrometry (MS) and confirmed as the titled compound. Furthermore, MS measurement result is shown.

Mass spectrum: 297,299.

Reference Example 6

4-Chloro-6-methyl-5-{[4-(trifluoromethyl)phenyl]ethynyl}pyrimidine

5-Iodo-6-methyl-4(3H)-pyrimidinone and [4-(trifluoromethyl)phenyl]ethynylzinc bromide were reacted in a solvent mixture of tetrahydrofuran and N,N-dimethylformamide (1:1) in the presence of tetrakis(triphenylphosphine)palladium while stirring under room temperature to heating to obtain a compound. The compound was mixed with POCl$_3$ and reacted while heating under reflux to obtain a target substance. The target substance was subjected to e.g., proton nuclear magnetic resonance spectrometry ($^1$H-NMR) and mass spectrometry (MS) and confirmed as the titled compound. Furthermore, MS measurement result is shown.

Mass spectrum: 297,299.

Reference Example 7

4-Chloro-6-methyl-5-{[4-(trifluoromethyl)phenyl]ethynyl}pyrimidine

A target substance was obtained by applying the methods described in Reference Example 1 to Reference Example 6. The target substance was subjected to e.g., proton nuclear magnetic resonance spectrometry ($^1$H-NMR) and mass spectrometry (MS) and confirmed as the titled compound. Furthermore, MS measurement result is shown.

Mass spectrum: 297,299.

Reference Example 8

4-Amino-6-methyl-5-{[4-(trifluoromethyl)phenyl]ethynyl}pyrimidine

A mixture of 4-chloro-6-methyl-5-{[4-(trifluoromethyl)phenyl]ethynyl}pyrimidine and ethanol was saturated with ammonia gas and reacted under heating in a shield tube to obtain a target substance. The target substance was subjected to e.g., proton nuclear magnetic resonance spectrometry ($^1$H-NMR) and mass spectrometry (MS) and confirmed as the titled compound. Furthermore, MS measurement result is shown.

Mass spectrum: 278.

Reference Example 9

4-Chloro-2,6-dimethyl-5-{[4-(trifluoromethyl)phenyl]ethynyl}pyrimidine

4-Chloro-2,6-dimethyl-5-iodopyrimidine and 4-ethynyl-α,α,α-trifluorotoluene were reacted in toluene in the presence of dichlorobis(triphenylphosphine)palladium, cuprous iodide and triethylamine while stirring under room temperature to heating to obtain a target substance. The target substance was subjected to e.g., proton nuclear magnetic resonance spectrometry ($^1$H-NMR) and mass spectrometry (MS) and confirmed as the titled compound. Furthermore, MS measurement result is shown.

Mass spectrum: 311,313.

Reference Example 10

4-Chloro-2,6-dimethyl-5-{[4-(trifluoromethyl)phenyl]ethynyl}pyrimidine 2,6-Dimethyl-5-iodo-4(3H)-pyrimidinone and 4-ethynyl-α,α,α-trifluorotoluene were reacted in toluene in the presence of dichlorobis(triphenylphosphine)palladium, cuprous iodide, and triethylamine while stirring under room temperature to heating to obtain a compound. The compound was mixed with POCl$_3$ and reacted while heating under reflux to obtain a target substance. The target substance was subjected to e.g., proton nuclear magnetic resonance spectrometry ($^1$H-NMR) and mass spectrometry (MS) and confirmed as the titled compound. Furthermore, MS measurement result is shown.

Mass spectrum: 311,313.

Reference Example 11

4-Amino-2,6-dimethyl-5-{[4-(trifluoromethyl)phenyl]ethynyl}pyrimidine

A mixture of 4-chloro-2,6-dimethyl-5-{[4-(trifluoromethyl)phenyl]ethynyl}pyrimidine and ethanol was saturated with ammonia gas and reacted under heating in a shield tube to obtain a target substance. The target substance was subjected to e.g., proton nuclear magnetic resonance spectrometry ($^1$H-NMR) and mass spectrometry (MS) and confirmed as the titled compound. Furthermore, MS measurement result is shown.

Mass spectrum: 292.

Example 1

Ethyl 5-{6-methyl-5-{[4-(trifluoromethyl)phenyl]ethynyl}pyrimidin-4-ylaminomethyl}-2-furancarboxylate [Compound No. 1]

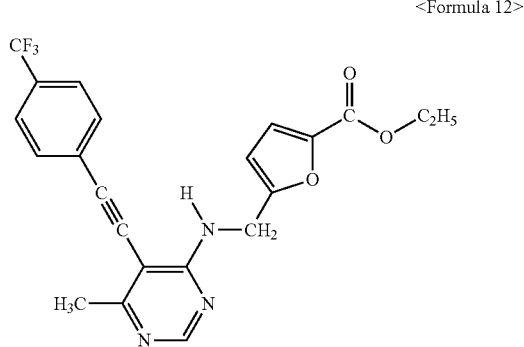 [SMILES: CCOC(=O)c1ccc(CNc2ncnc(C)c2C#Cc2ccc(C(F)(F)F)cc2)o1]

<Formula 12>

A mixture of 4-amino-6-methyl-5-{[4-(trifluoromethyl)phenyl]ethynyl}pyrimidine (2 g), triethylamine (0.76 g), ethyl 5-chloromethyl-2-furancarboxylate (1.4 g) and dichloromethane (60 ml) was heated to reflux while stirring for 72 hours. The mixture thus obtained was concentrated under reduced pressure. After the resultant residue was washed with water added thereto, an organic phase was dried over anhydrous sodium sulfate and then evaporated. The evaporation residue was purified by column chromatography to obtain a target substance (0.5 g). The target substance was subjected to e.g., proton nuclear magnetic resonance spectrometry ($^1$H-NMR) and mass spectrometry (MS) and confirmed as the titled compound. Furthermore, MS measurement result is shown.

Mass spectrum: 430.

Example 2

Ethyl 5-(6-methyl-5-{[4-(trifluoromethyl)phenyl]ethynyl}pyrimidin-4-ylaminomethyl)-2-furancarboxylate A mixture of 4-amino-6-methyl-5-{[4-(trifluoromethyl)phenyl]ethynyl}pyrimidine (2 g), triethylamine (0.76 g), ethyl 5-chloromethyl-2-furancarboxylate (1.4 g) and toluene (60 ml) was heated to reflux while stirring for 10 hours. The mixture thus obtained was concentrated under reduced pressure. After the resultant residue was washed with water added thereto, an organic phase was dried over anhydrous sodium sulfate and evaporated. The resultant residue was purified by column chromatography to obtain a target substance (0.6 g). The target substance was subjected to e.g., proton nuclear magnetic resonance spectrometry ($^1$H-NMR) and mass spectrometry (MS) and confirmed as the titled compound. Furthermore, MS measurement result is shown.

Mass spectrum: 430.

Example 3

Ethyl 5-(6-methyl-5-{[4-(trifluoromethyl)phenyl]ethynyl}pyrimidin-4-ylaminomethyl)-2-furancarboxylate A mixture of 4-amino-6-methyl-5-{[4-(trifluoromethyl)phenyl]ethynyl}pyrimidine (2.8 g), ethyl 5-chloromethyl-2-furancarboxylate (1.8 g), potassium carbonate (2.1 g) and N,N-dimethylformamide (120 ml) was heated while stirring at 70° C. for 15 hours. The mixture thus obtained was concentrated under reduced pressure. To the resultant residue, water was added. After extraction was performed with chloroform, an organic phase was dried over anhydrous sodium sulfate and then evaporated. The evaporated residue was purified by column chromatography to obtain a target substance (1 g). The target substance was subjected to e.g., proton nuclear magnetic resonance spectrometry ($^1$H-NMR) and mass spectrometry (MS) and confirmed as the titled compound. Furthermore, MS measurement result is shown.

Mass spectrum: 430.

Example 4

Ethyl 5-(6-methyl-5-{[4-(trifluoromethyl)phenyl]ethynyl}pyrimidin-4-ylaminomethyl)-2-furancarboxylate A mixture of 4-amino-6-methyl-5-{[4-(trifluoromethyl)phenyl]ethynyl}pyrimidine (2.8 g), ethyl 5-chloromethyl-2-furancarboxylate (1.8 g), potassium carbonate (2.1 g) and toluene (60 ml) was heated while stirring at 70° C. for 4 hours. The mixture thus obtained was concentrated under reduced pressure. To the resultant residue, water was added. After extraction was performed with dichloromethane, an organic phase was dried over anhydrous sodium sulfate and evaporated. The resultant residue was purified by column chromatography to obtain a target substance (0.9 g). The target substance was subjected to e.g., proton nuclear magnetic resonance spectrometry ($^1$H-NMR) and mass spectrometry (MS) and confirmed as the titled compound. Furthermore, MS measurement result is shown.

Mass spectrum: 430.

Example 5

Ethyl 5-(6-methyl-5-{[4-(trifluoromethyl)phenyl]ethynyl}pyrimidin-4-ylaminomethyl)-2-furancarboxylate A mixture of 4-amino-6-methyl-5-{[4-(trifluoromethyl)phenyl]ethynyl}pyrimidine (2.8 g), ethyl 5-chloromethyl-2-furancarboxylate (1.8 g), sodium hydrogencarbonate (1 g) and N,N-dimethylformamide (120 ml) was heated while stirring at 80° C. for 12 hours. The mixture thus obtained was concentrated under reduced pressure. To the resultant residue, water was added. After extraction was performed with ethyl acetate, an organic phase was dried over anhydrous sodium sulfate and evaporated. The resultant residue was purified by column chromatography to obtain a target substance (0.8 g). The target substance was subjected to e.g., proton nuclear magnetic resonance spectrometry ($^1$H-NMR) and mass spectrometry (MS) and confirmed as the titled compound. Furthermore, MS measurement result is shown.

Mass spectrum: 430.

Example 6

Ethyl 5-(6-methyl-5-{[4-(trifluoromethyl)phenyl] ethynyl}pyrimidin-4-ylaminomethyl)-2-furancarboxylate The method described in Example 1 was repeated except that ethyl 5-bromomethyl-2-furancarboxylate was used in place of ethyl 5-chloromethyl-2-furancarboxylate to obtain a target substance. The target substance was subjected to e.g., proton nuclear magnetic resonance spectrometry ($^1$H-NMR) and mass spectrometry (MS) and confirmed as the titled compound. Furthermore, MS measurement result is shown.

Mass spectrum: 430.

Example 7

Ethyl 5-(6-methyl-5-{[4-(trifluoromethyl)phenyl] ethynyl}pyrimidin-4-ylaminomethyl)-2-furancarboxylate The method described in Example 2 was repeated except that ethyl 5-bromomethyl-2-furancarboxylate was used in place of ethyl 5-chloromethyl-2-furancarboxylate to obtain a target substance. The target substance was subjected to e.g., proton nuclear magnetic resonance spectrometry ($^1$H-NMR) and mass spectrometry (MS) and confirmed as the titled compound. Furthermore, MS measurement result is shown.

Mass spectrum: 430.

Example 8

Ethyl 5-(6-methyl-5-{[4-(trifluoromethyl)phenyl] ethynyl}pyrimidin-4-ylaminomethyl)-2-furancarboxylate The method described in Example 3 was repeated except that ethyl 5-bromomethyl-2-furancarboxylate was used in place of ethyl 5-chloromethyl-2-furancarboxylate to obtain a target substance. The target substance was subjected to e.g., proton nuclear magnetic resonance spectrometry ($^1$H-NMR) and mass spectrometry (MS) and confirmed as the titled compound. Furthermore, MS measurement result is shown.

Mass spectrum: 430.

Example 9

Ethyl 5-(6-methyl-5-{[4-(trifluoromethyl)phenyl] ethynyl}pyrimidin-4-ylaminomethyl)-2-furancarboxylate The method described in Example 4 was repeated except that ethyl 5-bromomethyl-2-furancarboxylate was used in place of ethyl 5-chloromethyl-2-furancarboxylate to obtain a target substance. The target substance was subjected to e.g., proton nuclear magnetic resonance spectrometry ($^1$H-NMR) and mass spectrometry (MS) and confirmed as the titled compound. Furthermore, MS measurement result is shown.

Mass spectrum: 430.

Example 10

Ethyl 5-(6-methyl-5-{[4-(trifluoromethyl)phenyl] ethynyl}pyrimidin-4-ylaminomethyl)-2-furancarboxylate The method described in Example 5 was repeated except that ethyl 5-bromomethyl-2-furancarboxylate was used in place of ethyl 5-chloromethyl-2-furancarboxylate to obtain a target substance. The target substance was subjected to e.g., proton nuclear magnetic resonance spectrometry ($^1$H-NMR) and mass spectrometry (MS) and confirmed as the titled compound. Furthermore, MS measurement result is shown.

Mass spectrum: 430.

Example 11

Methyl 5-(6-methyl-5-{[4-(trifluoromethyl)phenyl] ethynyl}pyrimidin-4-ylaminomethyl)-2-furancarboxylate [Compound No. 2]

[Formula 13]

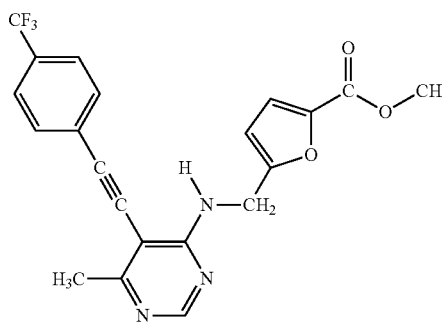

The method described in Example 1 was repeated except that methyl 5-chloromethyl-2-furancarboxylate was used in place of ethyl 5-chloromethyl-2-furancarboxylate to obtain a target substance. The target substance was subjected to e.g., proton nuclear magnetic resonance spectrometry ($^1$H-NMR) and mass spectrometry (MS) and confirmed as the titled compound. Furthermore, MS measurement result is shown.

Mass spectrum: 416.

Example 12

Methyl 5-(6-methyl-5-{[4-(trifluoromethyl)phenyl] ethynyl}pyrimidin-4-ylaminomethyl)-2-furancarboxylate The method described in Example 2 was repeated except that methyl 5-chloromethyl-2-furancarboxylate was used in place of ethyl 5-chloromethyl-2-furancarboxylate to obtain a target substance. The target substance was subjected to e.g., proton nuclear magnetic resonance spectrometry ($^1$H-NMR) and mass spectrometry (MS) and confirmed as the titled compound. Furthermore, MS measurement result is shown.

Mass spectrum: 416.

Example 13

Methyl 5-(6-methyl-5-{[4-(trifluoromethyl)phenyl]
ethynyl}pyrimidin-4-ylaminomethyl)-2-furancar-
boxylate The method described in Example 3 was repeated except that methyl 5-chloromethyl-2-furancarboxylate was used in place of ethyl 5-chloromethyl-2-furancarboxylate to obtain a target substance. The target substance was subjected to e.g., proton nuclear magnetic resonance spectrometry ($^1$H-NMR) and mass spectrometry (MS) and confirmed as the titled compound. Furthermore, MS measurement result is shown.
Mass spectrum: 416.

Example 14

Methyl 5-(6-methyl-5-{[4-(trifluoromethyl)phenyl]
ethynyl}pyrimidin-4-ylaminomethyl)-2-furancar-
boxylate The method described in Example 4 was repeated except that methyl 5-chloromethyl-2-furancarboxylate was used in place of ethyl 5-chloromethyl-2-furancarboxylate to obtain a target substance. The target substance was subjected to e.g., proton nuclear magnetic resonance spectrometry ($^1$H-NMR) and mass spectrometry (MS) and confirmed as the titled compound. Furthermore, MS measurement result is shown.
Mass spectrum: 416.

Example 15

Methyl 5-(6-methyl-5-{[4-(trifluoromethyl)phenyl]
ethynyl}pyrimidin-4-ylaminomethyl)-2-furancar-
boxylate The method described in Example 5 was repeated except that methyl 5-chloromethyl-2-furancarboxylate was used in place of ethyl 5-chloromethyl-2-furancarboxylate to obtain a target substance. The target substance was subjected to e.g., proton nuclear magnetic resonance spectrometry ($^1$H-NMR) and mass spectrometry (MS) and confirmed as the titled compound. Furthermore, MS measurement result is shown.
Mass spectrum: 416.

Example 16

Methyl 5-(6-methyl-5-{[4-(trifluoromethyl)phenyl]
ethynyl}pyrimidin-4-ylaminomethyl)-2-furancar-
boxylate The method described in Example 1 was repeated except that methyl 5-bromomethyl-2-furancarboxylate was used in place of ethyl 5-chloromethyl-2-furancarboxylate to obtain a target substance. The target substance was subjected to e.g., proton nuclear magnetic resonance spectrometry ($^1$H-NMR) and mass spectrometry (MS) and confirmed as the titled compound. Furthermore, MS measurement result is shown.
Mass spectrum: 416.

Example 17

Methyl 5-(6-methyl-5-{[4-(trifluoromethyl)phenyl]
ethynyl}pyrimidin-4-ylaminomethyl)-2-furancar-
boxylate The method described in Example 2 was repeated except that methyl 5-bromomethyl-2-furancarboxylate was used in place of ethyl 5-chloromethyl-2-furancarboxylate to obtain a target substance. The target substance was subjected to e.g., proton nuclear magnetic resonance spectrometry ($^1$H-NMR) and mass spectrometry (MS) and confirmed as the titled compound. Furthermore, MS measurement result is shown.
Mass spectrum: 416.

Example 18

Methyl 5-(6-methyl-5-{[4-(trifluoromethyl)phenyl]
ethynyl}pyrimidin-4-ylaminomethyl)-2-furancar-
boxylate The method described in Example 3 was repeated except that methyl 5-bromomethyl-2-furancarboxylate was used in place of ethyl 5-chloromethyl-2-furancarboxylate to obtain a target substance. The target substance was subjected to e.g., proton nuclear magnetic resonance spectrometry ($^1$H-NMR) and mass spectrometry (MS) and confirmed as the titled compound. Furthermore, MS measurement result is shown.
Mass spectrum: 416.

Example 19

Methyl 5-(6-methyl-5-{[4-(trifluoromethyl)phenyl]
ethynyl}pyrimidin-4-ylaminomethyl)-2-furancar-
boxylate The method described in Example 4 was repeated except that methyl 5-bromomethyl-2-furancarboxylate was used in place of ethyl 5-chloromethyl-2-furancarboxylate to obtain a target substance. The target substance was subjected to e.g., proton nuclear magnetic resonance spectrometry ($^1$H-NMR) and mass spectrometry (MS) and confirmed as the titled compound. Furthermore, MS measurement result is shown.
Mass spectrum: 416.

Example 20

Methyl 5-(6-methyl-5-{[4-(trifluoromethyl)phenyl]
ethynyl}pyrimidin-4-ylaminomethyl)-2-furancar-
boxylate The method described in Example 5 was repeated except that methyl 5-bromomethyl-2-furancarboxylate was used in place of ethyl 5-chloromethyl-2-furancarboxylate to obtain a target substance. The target substance was subjected to e.g., proton nuclear magnetic resonance spectrometry ($^1$H-NMR) and mass spectrometry (MS) and confirmed as the titled compound. Furthermore, MS measurement result is shown.
Mass spectrum: 416.

Example 21

Ethyl 4-(6-methyl-5-{[4-(trifluoromethyl)phenyl]
ethynyl}pyrimidin-4-ylaminomethyl)benzoate The method described in any one of Example 1 to Example 5 was repeated except that ethyl (4-bromomethyl)benzoate or ethyl (4-chloromethyl)benzoate was used in place of ethyl 5-chloromethyl-2-furancarboxylate to obtain a target substance. The target substance was subjected to e.g., proton nuclear magnetic resonance spectrometry ($^1$H-NMR) and mass spectrometry (MS) and confirmed as the titled compound. Furthermore, MS measurement result is shown.
Mass spectrum: 440.

Example 22

Methyl 4-(6-methyl-5-{[4-(trifluoromethyl)phenyl]
ethynyl}pyrimidin-4-ylaminomethyl)benzoate The method described in any one of Example 1 to Example 5 was repeated except that methyl (4-bromomethyl)benzoate or methyl (4-chloromethyl)benzoate was used in place of ethyl 5-chloromethyl-2-furancarboxylate to obtain a target substance. The target substance was subjected to e.g., proton nuclear magnetic resonance spectrometry ($^1$H-NMR) and mass spectrometry (MS) and confirmed as the titled compound. Furthermore, MS measurement result is shown.

Mass spectrum: 426.

Example 23

Ethyl 4-(2,6-dimethyl-5-{[4-(trifluoromethyl)phenyl]
ethynyl}pyrimidin-4-ylaminomethyl)benzoate A mixture of 4-chloro-2,6-dimethyl-5-{[4-(trifluoromethyl)phenyl]ethynyl}pyrimidine (5.0 g), ethyl (4-aminomethyl)benzoate (3.8 g), triethylamine (2.8 ml) and toluene (150 ml) was heated to reflux while stirring for 5 hours. The mixture thus obtained was concentrated under reduced pressure. To the resultant residue, water was added. After extraction was performed with chloroform, an organic phase was dried over anhydrous sodium sulfate and evaporated. The evaporation residue was purified by column chromatography to obtain a target substance (1 g). The target substance was subjected to e.g., proton nuclear magnetic resonance spectrometry ($^1$H-NMR) and mass spectrometry (MS) and confirmed as the titled compound. Furthermore, MS measurement result is shown.

Mass spectrum: 454.

Example 24

Ethyl 5-(2,6-dimethyl-5-{[4-(trifluoromethyl)phenyl]
ethynyl}pyrimidin-4-ylaminomethyl)-2-furancarboxylate The method described in any one of Example 1 to Example 10 and Example 23 was repeated except that 4-amino-2,6-dimethyl-5-{[4-(trifluoromethyl)phenyl]ethynyl}pyrimidine was used in place of 4-amino-6-methyl-5-{[4-(trifluoromethyl)phenyl]ethynyl}pyrimidine or ethyl 5-aminomethyl-2-furancarboxylate was used in place of ethyl (4-aminomethyl)benzoate to obtain a target substance. The target substance was subjected to e.g., proton nuclear magnetic resonance spectrometry ($^1$H-NMR) and mass spectrometry (MS) and confirmed as the titled compound. Furthermore, MS measurement result is shown.

Mass spectrum: 444.

Example 25

Ethyl 5-(6-methyl-5-{[4-(trifluoromethyl)phenyl]
ethynyl}pyrimidin-4-ylaminomethyl)-2-furancarboxylate The method described in Example 23 was repeated except that 4-chloro-6-methyl-5-{[4-(trifluoromethyl)phenyl]ethynyl}pyrimidine was used in place of 4-chloro-2,6-dimethyl-5-{[4-(trifluoromethyl)phenyl]ethynyl}pyrimidine and ethyl 5-aminomethyl-2-furancarboxylate was used in place of ethyl (4-aminomethyl)benzoate to obtain a target substance. The target substance was subjected to e.g., proton nuclear magnetic resonance spectrometry ($^1$H-NMR) and mass spectrometry (MS) and confirmed as the titled compound. Furthermore, MS measurement result is shown.

Mass spectrum: 430.

Example 26

Methyl 5-(6-methyl-5-{[4-(trifluoromethyl)phenyl]
ethynyl}pyrimidin-4-ylaminomethyl)-2-furancarboxylate The method described in Example 23 was repeated except that 4-chloro-6-methyl-5-{[4-(trifluoromethyl)phenyl]ethynyl}pyrimidine was used in place of 4-chloro-2,6-dimethyl-5-{[4-(trifluoromethyl)phenyl]ethynyl}pyrimidine and methyl 5-aminomethyl-2-furancarboxylate was used in place of ethyl (4-aminomethyl)benzoate to obtain a target substance. The target substance was subjected to e.g., proton nuclear magnetic resonance spectrometry ($^1$H-NMR) and mass spectrometry (MS) and confirmed as the titled compound. Furthermore, MS measurement result is shown.

Mass spectrum: 416.

Preparation Example 1

Tablet

| | | |
|---|---|---|
| 1) Compound of the present invention or a pharmaceutically acceptable salt thereof | | 30 g |
| 2) Lactose | | 50 g |
| 3) Cornstarch | | 15 g |
| 4) Calcium carboxymethylcellulose | | 44 g |
| 5) Magnesium stearate | | 1 g |
| 1000 tablets | total | 140 g |

A total amount of substances 1), 2), 3) and 30 g of substance 4) are kneaded with water, dried under vacuum to form sized powder. To the sized powder, 14 g of substance 4) and 1 g of substance 5) are mixed and the resultant mixture is punched to form tablets by using a tablet machine. In this manner, 1000 tablets containing a compound of the present invention or a pharmaceutically acceptable salt thereof (30 mg per tablet) are obtained. If necessary, these tablets may be covered with sugar coating or film coating.

Preparation Example 2

Capsule

| | | |
|---|---|---|
| 1) Compound of the present invention or a pharmaceutically acceptable salt thereof | | 10 mg |
| 2) Lactose | | 167 mg |
| 3) Magnesium stearate | | 3 mg |
| 1 capsule | total | 180 mg |

Substances 1), 2) and 3) are mixed by a conventional method and thereafter, a gelatin capsule is filled with the mixture to prepare a capsule.

Preparation Example 3

Injection (10 mg/ml)

| | |
|---|---|
| 1) Compound of the present invention or a pharmaceutically acceptable salt thereof | 1.0% w/v |
| 2) Sodium phosphate | 3.6% w/v |
| 3) 0.1M Sodium hydroxide solution | 15.0% v/v |
| 4) Water for injection | balance to 100% |

INDUSTRIAL APPLICABILITY

Since a compound of the present invention or a pharmaceutically acceptable salt thereof has an anticancer effect and/or a tyrosine kinase inhibitory effect, low toxicity, good solubility and absorbability, it can be used in therapeutic or prophylactic treatment for cancer and/or disease in which tyrosine kinases are involved (e.g., in a warm-blooded animal). Examples of the disease in which tyrosine kinases are involved include diseases in which cell proliferation (particularly, e.g., cancer cell proliferation), vascularization and/or increased vascular permeability due to abnormal tyrosine kinase activities are involved. Furthermore, since a compound of the present invention or a pharmaceutically acceptable salt thereof, or a prodrug thereof specifically inhibits tyrosine kinase activities, it is useful as a therapeutic and/or prophylactic agent suppressing growth of cancer expressing receptors responsive to tyrosine kinases.

The invention claimed is:

1. A compound represented by general formula (1A):

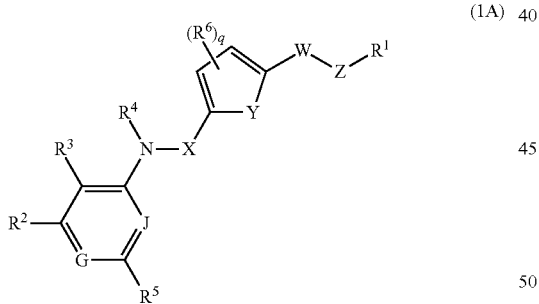

(1A)

wherein q is an integer selected from 0, 1, and 2; $R^1$ is a hydrogen atom, a halogen atom, a $C_{1-6}$ alkyl group, a $C_{1-6}$ haloalkyl group, a $C_{3-8}$ cycloalkyl group, a $C_{2-6}$ alkenyl group, a $C_{2-6}$ alkynyl group, a $C_{1-6}$ alkoxy $C_{1-6}$ alkyl group, an aralkyl group which may have one or more substituents, an aryl group which may have one or more substituents, an amino $C_{1-6}$ alkyl group which may have one or more substituents, a heterocyclic group which may have one or more substituents, or a heterocyclic $C_{1-6}$ alkyl group which may have one or more substituents; $R^2$ is a hydrogen atom, a halogen atom, a $C_{1-6}$ alkyl group, a $C_{1-6}$ haloalkyl group, a $C_{2-8}$ cycloalkyl group, a $C_{1-6}$ alkoxy $C_{1-6}$ alkyl group, a $C_{1-6}$ alkoxy group, an aryl group which may have one or more substituents, an aryl $C_{2-6}$ alkynyl group which may have one or more substituents, a $C_{2-6}$ alkenyl group which may have one or more substituents, or an aryl $C_{2-6}$ alkenyl group which may have one or more substituents; $R^3$ is a nitro group, a cyano group, a carbamoyl group, a $C_{1-6}$ haloalkyl group, a $C_{1-6}$ alkoxy group, a $C_{1-6}$ alkoxy $C_{1-6}$ alkyl group, a $C_{2-6}$ alkynyl group which may have one or more substituents, an aryl $C_{2-6}$ alkynyl group which may have one or more substituents, a $C_{2-6}$ alkenyl group which may have one or more substituents, an aryl $C_{2-6}$ alkenyl group which may have one or more substituents, a $C_{3-6}$ cycloalkenyl group, a $C_{4-6}$ cycloalkadienyl group, or a heterocyclic group which may have one or more substituents; $R^4$ is a hydrogen atom, a $C_{1-6}$ alkyl group, or a $C_{3-8}$ cycloalkyl group; $R^5$ is a hydrogen atom, a $C_{1-6}$ alkyl group, a $C_{3-8}$ cycloalkyl group, a $C_{1-6}$ alkoxy group, a $C_{1-6}$ alkylsulfanyl group, a $C_{1-6}$ alkylsulfinyl group, a $C_{1-6}$ alkylsulfonyl group, an amino group which may have one or more substituents, a $C_{1-6}$ haloalkyl group, a halogen atom, an aralkyl group which may have one or more substituents, a $C_{2-6}$ alkynyl group which may have one or more substituents, an aryl $C_{2-6}$ alkynyl group which may have one or more substituents, a $C_{2-6}$ alkenyl group which may have one or more substituents, an aryl $C_{2-6}$ alkenyl group which may have one or more substituents, a heterocyclic group which may have one or more substituents, or an aryl group which may have one or more substituents; $R^6$ is independently a $C_{1-6}$ alkoxy group, a halogen atom, a nitro group, a $C_{2-6}$ alkynyl group which may have one or more substituents, or a $C_{1-6}$ alkyl group; G and J are each independently a nitrogen atom; W is a single bond, C(O), S(O), S(O)$_2$ or an oxygen atom; X is a $C_{1-6}$ alkylene group; Y is an oxygen atom, or a sulfur atom; and Z is a single bond, an oxygen atom, O(CH$_2$)O, O(CH$_2$CH$_2$)O, O(CH$_2$CH$_2$CH$_2$)O, O(CH$_2$)C(O), O(CH$_2$CH$_2$)C(O), O(CH$_2$CH$_2$CH$_2$)C(O), NH, N(CH$_3$), or N(C$_2$H$_5$), or a pharmaceutically acceptable salt thereof.

2. A compound represented by general formula (2):

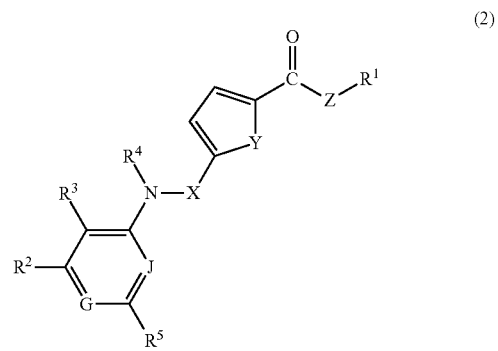

(2)

wherein $R^1$ is a hydrogen atom, a halogen atom, a $C_{1-6}$ alkyl group, a $C_{3-8}$ cycloalkyl group, a $C_{2-6}$ alkenyl group, a $C_{2-6}$ alkynyl group, an aralkyl group which may have one or more substituents, a $C_{1-6}$ alkoxy $C_{1-6}$ alkyl group, an aryl group which may have one or more substituents, an amino $C_{1-6}$ alkyl group which may have one or more substituents, a heterocyclic group which may have one or more substituents, or a heterocyclic $C_{1-6}$ alkyl group which may have one or more substituents; $R^2$ is a hydrogen atom, a halogen atom, a $C_{1-6}$ alkyl group, a $C_{1-6}$ haloalkyl group, a $C_{3-8}$ cycloalkyl group, a $C_{1-6}$ alkoxy $C_{1-6}$ alkyl group, a $C_{1-6}$ alkoxy group, an aryl group which may have one or more substituents, a $C_{2-6}$ alkynyl group which may have one or more substituents, an aryl $C_{2-6}$ alkynyl group which may have one or more substituents, a $C_{2-6}$ alkenyl group which may have one or more substituents, or an aryl $C_{2-6}$ alkenyl group which may have one or more substituents; $R^3$ is a hydrogen atom, a halogen atom, a nitro group, a cyano group, a carbamoyl group, a carboxyl group, a $C_{1-6}$ alkyl group, a $C_{1-6}$ haloalkyl group, a $C_{1-6}$ alkoxy group, a $C_{1-6}$ alkoxy $C_{1-6}$ alkyl group, a $C_{1-6}$ alkoxycarbonyl group, a $C_{2-6}$ alkynyl group which may have one or more substituents, an aryl $C_{2-6}$ alkynyl group which may have one or more substituents, a $C_{2-6}$ alkenyl group which may have one or more substituents, an aryl $C_{2-6}$ alkenyl group which may have one or more substituents, a heterocyclic group which may have one or more substituents, or an aryl group which may have one or more substituents; $R^4$ is a hydrogen atom, a $C_{1-6}$ alkyl group, or a $C_{3-8}$ cycloalkyl group; $R^5$ is a hydrogen atom, a $C_{1-6}$ alkyl group, a $C_{3-8}$ cycloalkyl group, a $C_{1-6}$ alkoxy group, a $C_{1-6}$ alkylsulfanyl group, a $C_{1-6}$ alkylsulfinyl group, a $C_{1-6}$ alkylsulfonyl group, an amino group which may have one or more substituents, a $C_{1-6}$ haloalkyl group, a halogen atom, an aralkyl group which may have one or more substituents, a $C_{2-6}$ alkynyl group which may have one or more substituents, an aryl $C_{2-6}$ alkynyl group which may have one or more substituents, a $C_{2-6}$ alkenyl group which may have one or more substituents, an aryl $C_{2-6}$ alkenyl group which may have one or more substituents, a heterocyclic group which may have one or more substituents, or an aryl group which may have one or more substituents; G is a nitrogen atom; J is a nitrogen atom; X is a $C_{1-6}$ alkylene group; Y is an oxygen atom, or a sulfur atom; and Z is a single bond, an oxygen atom, $O(CH_2)O$, $O(CH_2CH_2)O$, $O(CH_2CH_2CH_2)O$, $O(CH_2)C(O)$, $O(CH_2CH_2)C(O)$, $O(CH_2CH_2CH_2)C(O)$, NH, $N(CH_3)$, or $N(C_2H_5)$, or a pharmaceutically acceptable salt thereof.

3. A compound represented by general formula (3):

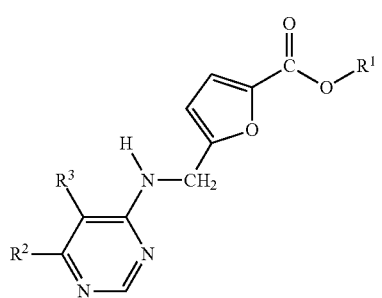

(3)

wherein $R^1$ is a hydrogen atom, a $C_{1-6}$ alkyl group, a $C_{3-8}$ cycloalkyl group, a $C_{2-6}$ alkenyl group, a $C_{2-6}$ alkynyl group, or an aralkyl group which may have one or more substituents; $R^2$ is a hydrogen atom, a halogen atom, a $C_{1-6}$ alkyl group, a $C_{1-6}$ haloalkyl group, a $C_{1-6}$ alkoxy $C_{1-6}$ alkyl group, a $C_{1-6}$ alkoxy group, an aryl group which may have one or more substituents, a $C_{2-6}$ alkynyl group which may have one or more substituents, an aryl $C_{2-6}$ alkynyl group which may have one or more substituents, a $C_{2-6}$ alkenyl group which may have one or more substituents, or an aryl $C_{2-6}$ alkenyl group which may have one or more substituents; and $R^3$ is a hydrogen atom, a halogen atom, a cyano group, a carbamoyl group, a carboxyl group, a $C_{1-6}$ alkyl group, a $C_{1-6}$ haloalkyl group, a $C_{1-6}$ alkoxy group, a $C_{1-6}$ alkoxycarbonyl group, a $C_{2-6}$ alkynyl group which may have one or more substituents, an aryl $C_{2-6}$ alkynyl group which may have one or more substituents, an aryl $C_{2-6}$ alkenyl group which may have one or more substituents, a $C_{2-6}$ alkenyl group which may have one or more substituents, or an aryl group which may have one or more substituents, or a pharmaceutically acceptable salt thereof.

4. A compound represented by general formula (4):

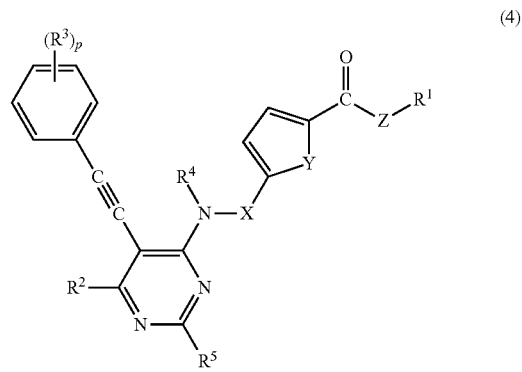

(4)

wherein p is an integer selected from 0, 1, 2 and 3; $R^1$ is a hydrogen atom, a $C_{1-6}$ alkyl group, a $C_{3-8}$ cycloalkyl group, a $C_{2-6}$ alkenyl group, a $C_{2-6}$ alkynyl group, an aralkyl group which may have one or more substituents, an amino $C_{1-6}$ alkyl group which may have one or more substituents, a heterocyclic group which may have one or more substituents, or a heterocyclic $C_{1-6}$ alkyl group which may have one or more substituents; $R^2$ is a hydrogen atom, a $C_{1-6}$ alkyl group, a $C_{1-6}$ haloalkyl group, or a halogen atom; $R^3$ is independently a halogen atom, a $C_{1-6}$ haloalkyl group, a $C_{1-6}$ alkyl group, a $C_{1-6}$ alkoxy group, or a $C_{1-6}$ haloalkoxy group; $R^4$ is a hydrogen atom or a $C_{1-6}$ alkyl group; $R^5$ is a hydrogen atom, a $C_{1-6}$ alkyl group, a $C_{3-8}$ cycloalkyl group, a $C_{1-6}$ haloalkyl group, or a halogen atom; X is a $C_{1-6}$ alkylene group; Y is an oxygen atom or a sulfur atom; and Z is a single bond, an oxygen atom, $O(CH_2)O$, $O(CH_2CH_2)O$, $O(CH_2)C(O)$, $O(CH_2CH_2)C(O)$, NH, $N(CH_3)$, or $N(C_2H_5)$, or a pharmaceutically acceptable salt thereof.

5. The compound or a pharmaceutically acceptable salt thereof according to claim 4, wherein $R^1$ is a hydrogen atom or a $C_{1-6}$ alkyl group; $R^2$ is a hydrogen atom or a $C_{1-6}$ alkyl group; $R^3$ is a halogen atom, a $C_{1-6}$ haloalkyl group, or a $C_{1-6}$ alkyl group; $R^5$ is a hydrogen atom or a $C_{1-6}$ alkyl group; and Z is an oxygen atom.

6. A compound represented by general formula (5):

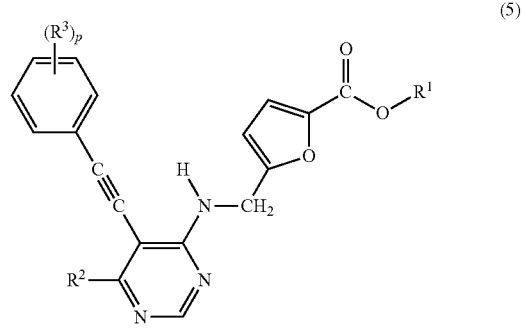

(5)

wherein p is an integer selected from 0, 1, 2 and 3, $R^1$ is a hydrogen atom or a $C_{1-6}$ alkyl group; $R^2$ is a hydrogen atom, a halogen atom, a $C_{1-6}$ alkyl group, or a $C_{1-6}$ haloalkyl group; and $R^3$ is independently a halogen atom, a $C_{1-6}$ alkyl group, or a $C_{1-6}$ haloalkyl group, or a pharmaceutically acceptable salt thereof.

7. The compound or a pharmaceutically acceptable salt thereof according to claim 6, wherein $R^2$ is a hydrogen atom or a $C_{1-6}$ alkyl group.

8. A compound represented by general formula (6):

wherein $R^1$ is a hydrogen atom or a $C_{1-6}$ alkyl group; $R^2$ is a hydrogen atom or a $C_{1-6}$ alkyl group; and $R^3$ is a hydrogen atom, a halogen atom, a $C_{1-6}$ alkyl group, or a $C_{1-6}$ haloalkyl group, or a pharmaceutically acceptable salt thereof.

9. The compound or a pharmaceutically acceptable salt thereof according to claim 4, wherein $R^1$ is a $C_{1-6}$ alkyl group; $R^2$ is a $C_{1-6}$ alkyl group; and $R^3$ is a halogen atom or a $C_{1-6}$ haloalkyl group.

10. The compound or a pharmaceutically acceptable salt thereof according to claim 4, wherein $R^1$ is a methyl group or an ethyl group; $R^2$ is a methyl group or an ethyl group; and $R^3$ is a fluorine atom, a chlorine atom, or a trifluoromethyl group.

11. A compound represented by general formula (7):

wherein $R^1$ is a methyl group or an ethyl group; and $R^2$ is a methyl group or an ethyl group, or a pharmaceutically acceptable salt thereof.

12. A compound selected from the group consisting of:
methyl 5-(6-methyl-5-{[4-(trifluoromethyl)phenyl]ethynyl}pyrimidin-4-ylaminomethyl)-2-furancarboxylate; and
ethyl 5-(6-methyl-5-{[4-(trifluoromethyl)phenyl]ethynyl}pyrimidin-4-ylaminomethyl)-2-furancarboxylate, or a pharmaceutically acceptable salt thereof.

13. A compound selected from the group consisting of:
methyl 5-(5-{[4-(trifluoromethyl)phenyl]ethynyl}pyrimidin-4-ylaminomethyl)-2-furancarboxylate; and
ethyl 5-(5-{[4-(trifluoromethyl)phenyl]ethynyl}pyrimidin-4-ylaminomethyl)-2-furancarboxylate, or a pharmaceutically acceptable salt thereof.

14. A compound selected from the group consisting of:
methyl 5-(2-isopropyl-6-methyl-5-{[4-(trifluoromethyl)phenyl]ethynyl}pyrimidin-4-ylaminomethyl)-2-furancarboxylate;
ethyl 5-(2-isopropyl-6-methyl-5-{[4-(trifluoromethyl)phenyl]ethynyl}pyrimidin-4-ylaminomethyl)-2-furancarboxylate;
methyl 5-(2,6-dimethyl-5-{[4-(trifluoromethyl)phenyl]ethynyl}pyrimidin-4-ylaminomethyl)-2-furancarboxylate; and
ethyl 5-(2,6-dimethyl-5-{[4-(trifluoromethyl)phenyl]ethynyl}pyrimidin-4-ylaminomethyl)-2-furancarboxylate, or a pharmaceutically acceptable salt thereof.

15. A pharmaceutical composition containing the compound or a pharmaceutically acceptable salt thereof according to claim 1.

16. The compound or a pharmaceutically acceptable salt thereof according to claim 6, wherein $R^1$ is a $C_{1-6}$ alkyl group; $R^2$ is a $C_{1-6}$ alkyl group; and $R^3$ is a halogen atom or a $C_{1-6}$ haloalkyl group.

17. The compound or a pharmaceutically acceptable salt thereof according to claim 6, wherein $R^1$ is a methyl group or an ethyl group; $R^2$ is a methyl group or an ethyl group; and $R^3$ is a fluorine atom, a chlorine atom, or a trifluoromethyl group.

18. The compound or a pharmaceutically acceptable salt thereof according to claim 8, wherein $R^1$ is a $C_{1-6}$ alkyl group; $R^2$ is a $C_{1-6}$ alkyl group; and $R^3$ is a halogen atom or a $C_{1-6}$ haloalkyl group.

19. The compound or a pharmaceutically acceptable salt thereof according to claim 8, wherein $R^1$ is a methyl group or an ethyl group; $R^2$ is a methyl group or an ethyl group; and $R^3$ is a fluorine atom, a chlorine atom, or a trifluoromethyl group.

* * * * *

UNITED STATES PATENT AND TRADEMARK OFFICE
CERTIFICATE OF CORRECTION

PATENT NO. : 8,895,565 B2
APPLICATION NO. : 13/201201
DATED : November 25, 2014
INVENTOR(S) : Tetsuya Nishio It is certified that error appears in the above-identified patent and that said Letters Patent is hereby corrected as shown below:

In the Specification

Column 14, lines 17-18, "an N-methylpiperidin-group" should read
--an N-methylpiperidin-2-ylmethyl group--.

Column 16, lines 21-22, insert --a (4-chlorophenyl)ethynyl group,-- between
"a (3-chlorophenyl)ethynyl group," and "a (4-fluorophenyl)ethynyl group,".

Column 24, lines 27 and 30 and Column 28, lines 1, 6 and 11, "compound (II)", each occurrence, should read --compound (11)--.

In the Claims

Column 47, line 53 (Claim 1), "from 0, 1, and 2" should read --from 0, 1 and 2--.

Column 47, line 64 (Claim 1), "a $C_{2-8}$ cycloalkyl group" should read --a $C_{3-8}$ cycloalkyl group--.

Column 48, line 1 (Claim 1), insert --a $C_{2-6}$ alkynyl group which may have one or more substituents,-- between "one or more substituents," and "a $C_{2-6}$ alkenyl group which".

Column 48, line 36 (Claim 1), "$N(CH_2)$" should read --$N(CH_3)$--.

Signed and Sealed this
Second Day of June, 2015

Michelle K. Lee
*Director of the United States Patent and Trademark Office*